(12) United States Patent
Azure

(10) Patent No.: US 9,308,039 B2
(45) Date of Patent: Apr. 12, 2016

(54) ABLATION PROBE WITH DEPLOYABLE ELECTRODES

(75) Inventor: Larry Azure, La Conner, WA (US)

(73) Assignee: LaZure Scientific, Inc., Issaquah, WA (US)

( * ) Notice: Subject to any disclaimer, the term of this patent is extended or adjusted under 35 U.S.C. 154(b) by 953 days.

(21) Appl. No.: 13/344,373

(22) Filed: Jan. 5, 2012

(65) Prior Publication Data
US 2012/0232550 A1 Sep. 13, 2012

Related U.S. Application Data

(63) Continuation of application No. 11/855,940, filed on Sep. 14, 2007, now Pat. No. 8,109,926.

(60) Provisional application No. 60/863,484, filed on Oct. 30, 2006, provisional application No. 60/825,660, filed on Sep. 14, 2006.

(51) Int. Cl.
*A61B 18/14* (2006.01)
*A61N 1/06* (2006.01)
*A61B 18/00* (2006.01)

(52) U.S. Cl.
CPC .......... *A61B 18/1477* (2013.01); *A61B 18/1492* (2013.01); *A61N 1/06* (2013.01); *A61B 2018/00577* (2013.01); *A61B 2018/143* (2013.01); *A61B 2018/1407* (2013.01); *A61B 2018/1425* (2013.01); *A61B 2018/1475* (2013.01)

(58) Field of Classification Search
CPC ........... A61B 18/1477; A61B 18/1492; A61B 2018/1407; A61B 2018/1425; A61B 2018/1475; A61B 2018/142; A61B 2018/00577
USPC ............. 606/27–31, 41, 48–50; 607/101, 102
See application file for complete search history.

(56) References Cited

U.S. PATENT DOCUMENTS

| | | | |
|---|---|---|---|
| 3,991,770 | A | 11/1976 | LeVeen |
| 4,016,886 | A | 4/1977 | Doss et al. |
| 4,346,715 | A | 8/1982 | Gammell |
| 4,448,198 | A | 5/1984 | Turner |

(Continued)

FOREIGN PATENT DOCUMENTS

| | | |
|---|---|---|
| JP | 2002-253569 A | 9/2002 |
| WO | WO 96/04860 A1 | 2/1996 |

(Continued)

OTHER PUBLICATIONS

Aoyagi et al., "Effects of Moderate Hyperthermia on the Rabbit Sacroma Model," Neurol. Med. Chir. (Tokyo) 43:105-111 (2003).

(Continued)

*Primary Examiner* — Michael Peffley
(74) *Attorney, Agent, or Firm* — Wilson Sonsini Goodrich & Rosati

(57) ABSTRACT

The present invention provides systems, devices and related methods for applying electric fields for cancerous cell destruction and tissue ablation. A method can include advancing an ablation probe into a patient; deploying a guide from the delivery member along a guide tissue penetration path, deploying an electrode from the guide along an electrode tissue penetration path, and establishing current flow within the target tissue.

18 Claims, 20 Drawing Sheets

(56) References Cited

U.S. PATENT DOCUMENTS

| | | | |
|---|---|---|---|
| 4,676,258 A | 6/1987 | Inokuchi et al. | |
| 4,732,161 A | 3/1988 | Azam et al. | |
| 4,763,671 A | 8/1988 | Goffinet | |
| 4,821,725 A | 4/1989 | Azam et al. | |
| 4,860,752 A | 8/1989 | Turner | |
| 5,277,201 A | 1/1994 | Stern | |
| 5,370,677 A | 12/1994 | Rudie et al. | |
| 5,472,441 A | 12/1995 | Edwards et al. | |
| 5,536,267 A * | 7/1996 | Edwards et al. | 606/41 |
| 5,630,426 A | 5/1997 | Eggers et al. | |
| 5,681,282 A | 10/1997 | Eggers et al. | |
| 5,807,395 A | 9/1998 | Mulier et al. | |
| 5,810,804 A | 9/1998 | Gough et al. | |
| 5,827,276 A | 10/1998 | LeVeen et al. | |
| 5,855,576 A | 1/1999 | LeVeen et al. | |
| 5,863,290 A * | 1/1999 | Gough et al. | 606/41 |
| 5,868,740 A | 2/1999 | LeVeen et al. | |
| 5,935,123 A | 8/1999 | Edwards et al. | |
| 5,957,922 A | 9/1999 | Imran | |
| 5,968,041 A | 10/1999 | Edwards | |
| 5,993,447 A | 11/1999 | Blewett et al. | |
| 6,050,992 A | 4/2000 | Nichols | |
| 6,056,744 A | 5/2000 | Edwards | |
| 6,071,280 A | 6/2000 | Edwards et al. | |
| 6,080,150 A | 6/2000 | Gough | |
| 6,090,105 A | 7/2000 | Zepeda et al. | |
| 6,136,020 A | 10/2000 | Faour | |
| 6,148,236 A | 11/2000 | Dann | |
| 6,149,620 A | 11/2000 | Baker et al. | |
| 6,212,433 B1 | 4/2001 | Behl | |
| 6,231,570 B1 | 5/2001 | Tu et al. | |
| 6,235,023 B1 | 5/2001 | Lee et al. | |
| 6,246,912 B1 | 6/2001 | Sluijter et al. | |
| 6,296,638 B1 | 10/2001 | Davison et al. | |
| 6,402,742 B1 | 6/2002 | Blewett et al. | |
| 6,419,653 B2 | 7/2002 | Edwards et al. | |
| 6,440,127 B2 | 8/2002 | McGovern et al. | |
| 6,477,426 B1 | 11/2002 | Fenn et al. | |
| 6,517,534 B1 | 2/2003 | McGovern et al. | |
| 6,537,272 B2 | 3/2003 | Christopherson et al. | |
| 6,652,515 B1 | 11/2003 | Maguire et al. | |
| 6,682,555 B2 | 1/2004 | Cioanta et al. | |
| 6,738,663 B2 | 5/2004 | Schroeppel et al. | |
| 6,743,226 B2 | 6/2004 | Cosman et al. | |
| 6,850,804 B2 | 2/2005 | Eggers et al. | |
| 6,853,864 B2 | 2/2005 | Litovitz | |
| 6,866,624 B2 | 3/2005 | Chornenky et al. | |
| 6,868,289 B2 | 3/2005 | Palti | |
| 6,892,099 B2 | 5/2005 | Jaafar et al. | |
| 6,939,346 B2 | 9/2005 | Kannenberg et al. | |
| 6,944,504 B1 | 9/2005 | Arndt et al. | |
| 6,958,064 B2 | 10/2005 | Rioux et al. | |
| 6,962,587 B2 * | 11/2005 | Johnson et al. | 606/41 |
| 6,993,394 B2 | 1/2006 | Eggers et al. | |
| 6,994,706 B2 | 2/2006 | Chornenky et al. | |
| 7,016,725 B2 | 3/2006 | Palti | |
| 7,053,063 B2 | 5/2006 | Rubinsky et al. | |
| 7,089,054 B2 | 8/2006 | Palti | |
| 7,135,029 B2 | 11/2006 | Makin et al. | |
| 7,136,699 B2 | 11/2006 | Palti | |
| 7,146,210 B2 | 12/2006 | Palti | |
| 7,238,182 B2 | 7/2007 | Swoyer et al. | |
| 7,311,708 B2 | 12/2007 | McClurken | |
| 7,333,852 B2 | 2/2008 | Palti | |
| 7,680,543 B2 | 3/2010 | Azure | |
| 7,722,606 B2 | 5/2010 | Azure | |
| 8,048,067 B2 * | 11/2011 | Davalos et al. | 606/32 |
| 8,109,926 B2 | 2/2012 | Azure | |
| 8,251,986 B2 | 8/2012 | Chornenky et al. | |
| 8,603,087 B2 | 12/2013 | Rubinsky et al. | |
| 2002/0058933 A1 | 5/2002 | Christopherson et al. | |
| 2002/0077627 A1 | 6/2002 | Johnson et al. | |
| 2002/0077676 A1 | 6/2002 | Schroeppel et al. | |
| 2002/0082610 A1 | 6/2002 | Cioanta et al. | |
| 2003/0130575 A1 | 7/2003 | Desai | |
| 2003/0130711 A1 | 7/2003 | Pearson et al. | |
| 2003/0150372 A1 | 8/2003 | Palti | |
| 2003/0233099 A1 | 12/2003 | Danaek et al. | |
| 2004/0068297 A1 | 4/2004 | Palti | |
| 2004/0087939 A1 | 5/2004 | Eggers et al. | |
| 2004/0116952 A1 | 6/2004 | Sakurai et al. | |
| 2004/0176804 A1 | 9/2004 | Palti | |
| 2004/0230190 A1 | 11/2004 | Dahla et al. | |
| 2005/0171523 A1 | 8/2005 | Rubinsky et al. | |
| 2005/0171574 A1 | 8/2005 | Rubinsky et al. | |
| 2005/0209640 A1 | 9/2005 | Palti | |
| 2005/0209641 A1 | 9/2005 | Palti | |
| 2005/0209642 A1 | 9/2005 | Palti | |
| 2005/0222646 A1 | 10/2005 | Kroll et al. | |
| 2005/0234439 A1 | 10/2005 | Underwood | |
| 2005/0240173 A1 | 10/2005 | Palti | |
| 2005/0240228 A1 | 10/2005 | Palti | |
| 2005/0251126 A1 | 11/2005 | Gellman et al. | |
| 2005/0261672 A1 * | 11/2005 | Deem et al. | 606/41 |
| 2006/0079883 A1 | 4/2006 | Elmouelhi et al. | |
| 2006/0149226 A1 | 7/2006 | McCullagh et al. | |
| 2006/0149341 A1 | 7/2006 | Palti | |
| 2006/0155270 A1 | 7/2006 | Hancock et al. | |
| 2006/0167499 A1 | 7/2006 | Palti | |
| 2006/0217694 A1 | 9/2006 | Chin et al. | |
| 2006/0217703 A1 | 9/2006 | Chornenky et al. | |
| 2006/0233867 A1 | 10/2006 | Palti | |
| 2006/0237019 A1 | 10/2006 | Palti | |
| 2006/0241547 A1 | 10/2006 | Palti | |
| 2006/0241577 A1 | 10/2006 | Balbierz et al. | |
| 2006/0264752 A1 | 11/2006 | Rubinsky et al. | |
| 2006/0282122 A1 | 12/2006 | Palti | |
| 2006/0293730 A1 * | 12/2006 | Rubinsky et al. | 607/98 |
| 2007/0043345 A1 | 2/2007 | Davalos et al. | |
| 2007/0135879 A1 | 6/2007 | McIntyre et al. | |
| 2007/0225766 A1 | 9/2007 | Palti | |
| 2008/0033422 A1 | 2/2008 | Turner et al. | |
| 2011/0015630 A1 | 1/2011 | Azure | |

FOREIGN PATENT DOCUMENTS

| | | |
|---|---|---|
| WO | WO 00/13603 A1 | 3/2000 |
| WO | WO 02/32335 A1 | 4/2002 |
| WO | WO 02/089686 A1 | 11/2002 |
| WO | WO 2005/065284 A2 | 7/2005 |
| WO | WO 2005/065284 A3 | 11/2005 |
| WO | WO 2006/036706 A1 | 4/2006 |

OTHER PUBLICATIONS

Baronzio and Hager, "Medical Intelligence Unit—Hyperthermia in Cancer Treatment: A Primer," Landes Bioscience and Springer Science+Business Media LLC; ISBN:0-387-33440-8 (2006).

Chan et al., "Electrically Stimulated Cell Membrane Breakdown in Human Placenta TL and Lung Cancer Cell A549 in 3D Trap Arrays on Si Substrate," Device Research Conference, pp. 103-104 (Jun. 23-25, 2003).

Chang, D.C., "Design of protocols for electroporation and electrofusion: Selection of electrical parameters," in D. C. Chang, B. M. Chassy, J. A. Saunders and A. E. Sowers. (Ed.Eds.), Guide to electroporation and electrofusion. Academic Press, Inc., San Diego, pp. 429-455 (1992).

Chang, D.C., "Structure and dynamics of electric field-induced membrane pores as revealed by rapid-freezing electron microscopy," in D. C. Chang, B. M. Chassy, J. A. Saunders and A. E. Sowers. (Ed.Eds.), Guide to Electroporation and Electrofusion. Academic Press, Inc., San Diego, pp. 9-27 (1992).

Coss et al., "Effects of Hyperthermia (41.5°) on Chinese Hamster Ovary Cells Analyzed in Mitosis," Cancer Research 39:1911-1918 (1979).

Cucullo et al., "Very Low Intensity Alternating Current Decreases Cell Proliferation," GLIA 51:65-72 (2005).

DeFord et al., "Effective Estimation and Computer Ccontrol of Minimum Tumour Temperature During Conductive Interstitial Hyperthermia," Int. J. Hyperthermia 7:441-453 (1991).

Haemmerich and Wood, "Hepatic Radiofrequency Ablation at Low Frequencies Preferentially," Int. J. Hyperthermia 22:563-574 (2006).

(56) References Cited

OTHER PUBLICATIONS

Haemmerich, et al. RF ablation at audio frequencies preferentially targets tumor—a finite element study. Proceedings of the second joint EMBS/BMES Conf. Oct 23-26, 2002; 1797-1798.

International search report and written opinion dated Mar. 13, 2008 for PCT/US2007/078559.

International search report and written opinion dated Aug. 12, 2008 for PCT/US2007/078567.

International search report and written opinion dated Aug. 13, 2008 for PCT/US2007/078562.

Janigro et al., "Alternating Current Electrical Stimulation Enhanced Chemotherapy: a Novel Strategy to Bypass Multidrug Resistance in Tumor Cells," BMC Cancer 6:1-12 (2006).

Kirson et al., "Alternating Electric Fields Arrest Cell Proliferation in Animal Tumor Models and Human Brain Tumors," PNAS 104:10152-10157 (2007).

Kirson et al., "Disruption of Cancer Cell Replicatioin by Alternating Electric Fields," Cancer Res. 64:3288-3295 (2004).

Marmor et al., "Tumor Cure and Cell Survival After Localized Radiofrequency Heating," Cancer Research 37:879-883 (1977).

Miller et al., "Cancer Cells Ablation With Irreversible Electroporation," Technology in Cancer Research & Treatment 4:1-7 (2005).

Oleson et al., "Biological and Clinical Aspects of Hyperthermia in Cancer Therapy," Am J. Clin. Oncol. 11:368-380 (1988).

Pethig, R., "Dielectric Properties of Biological Materials: Biophysical and Medical Applications," IEEE Trans. EI 19(5): 453-473 (1984).

Proskuryakov et al., "Necrosis is an Active and Controlled Form of Programmed Cell Death," Biochemistry (Moscow) 67:387-408 (2002).

Rubinsky et al., "Irreversible Electroporation: a New Ablation Modality—Clinical Implications," Tech. Cancer Res. Treatment 6:1-12 (2007).

Shimm and Gerner, "Hyperthermia in the Treatment of Malignancies," in: Lehman, Justus F., Therapeutic Heat and Cold (Maryland, Williams & Wilkins, 1990), Ch. 14, pp. 674-699. ISBN 0-683-04908-9.

Stix, "Blockbuster—New Understanding of the Biology Behind a Successful Cancer Therapy May Lead to a Drug That Can Treat an Array of Solid Tumors," Scientific American, 294(5): 60-63 (May 2006).

Tello et al., "Electrochemical Therapy to Treat Cancer (In Vivo Treatment)," Proceedings of the 20th Annual International Conference of the IEEE EMBS, pp. 3524-3527 (Aug. 23-26, 2007).

Yi, "Cellular Ion Content Changes During and After Hyperthermia," Biochem Biophys. Res. Communic. 91:177-182 (1979).

Zimmermann, U., "Electric field-mediated fusion and related electrical phenomena," Biochim Biophys Acta 694(3): 227-277 (1982).

Zimmermann, U., et al. "Transcellular ion flow in *Escherichia coli* B and electrical sizing of bacterias," Biophys. J. 13(10): 1005-1013 (1973).

Zimmermann, U., et al., "Rotation of cells in an alternating electric field: the occurrence of a resonance frequency," Z. Naturforsch [C] 36(1-2): 173-177 (1981).

European search report and opinion dated Jan. 4, 2013 for EP Application No. 07842548.5.

* cited by examiner

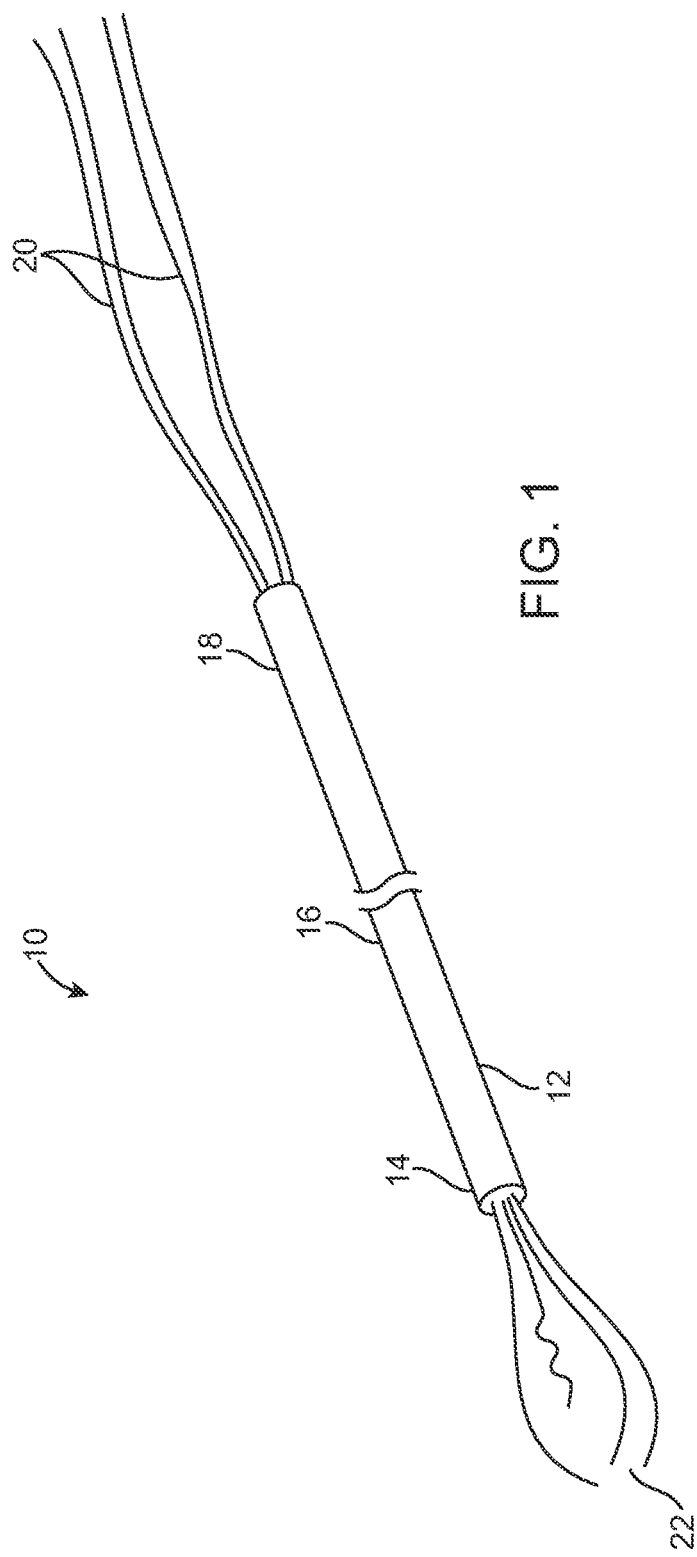

ABLATION PROBE WITH DEPLOYABLE ELECTRODES

CROSS-REFERENCES TO RELATED APPLICATIONS

This application is a continuation of U.S. patent application Ser. No. 11/855,940, filed Sep. 14, 2007, now U.S. Pat. No. 8,109,926, which issued on Feb. 7, 2012, which claims the benefit under 35 U.S.C. §119(e) of U.S. Provisional Patent Application No. 60/825,660, filed Sep. 14, 2006, and U.S. Provisional Patent Application No. 60/863,484, filed Oct. 30, 2006, the full disclosures of which are incorporated herein by reference.

This application is related to U.S. application Ser. No. 11/855,956, filed on Sep. 14, 2007, now U.S. Pat. No. 7,722,606 and U.S. application Ser. No. 11/855,977, filed on Sep. 14, 2007, now U.S. Pat. No. 7,680,543, the full disclosures of which are incorporated herein by reference.

BACKGROUND OF THE INVENTION

The present invention relates generally to electric field delivery to tissue regions. More specifically, the present invention relates to electric field delivery and ablation of target tissue regions, including cancerous cells and solid tumors, using improved ablation probes.

Current tissue ablation techniques rely on a high-frequency, hyper-thermia inducing electric current to the tissue of a patient (e.g., human, animal, etc.) as a means to remove unwanted tissue or lesions, staunch bleeding, or cut tissue. There has been increased interest and activity is the area of hyper-thermal ablation as a tool to treat cancer by heat-induced killing and/or removal of tumor tissue.

In hyper-thermal tumor ablation techniques, high-frequency RF (e.g., "RF thermal ablation") or microwave sources are used to heat tissue resulting in histological damage to the target tissue. In RF thermal ablation techniques, for example, high frequencies, including about 500 kHz and greater, are used to cause ionic agitation and frictional (e.g., resistive) heating to tissue surrounding a positioned electrode. Lethal damage to tissue (e.g., denaturation of tissue proteins) occurs at temperatures in excess of about 47 degrees C., though heat generated near electrodes in RF thermal ablation can reach temperatures up to or exceeding about 100 degrees C.

Numerous methods and devices are taught using hyper-thermal or heat-induced cancer tissue destruction. However, a significant limitation of RF induced, hyper-thermal ablation is the difficulty of localizing the heat-induced damage to targeted cancerous tissue while limiting histological damage and destruction to surrounding healthy, non-target tissue.

Thus, there is a need for minimally invasive ablation techniques that more selectively destroy targeted tissue while minimizing damage to non-target tissue.

BRIEF SUMMARY OF THE INVENTION

The present invention provides systems, devices and related methods for applying electric fields for cancerous cell destruction and tissue ablation, e.g., non-thermal tissue ablation. Devices of the present invention will generally be designed to advance an electrode or plurality of electrodes to a target tissue region and apply an electric field to the target tissue region. The electrode or plurality thereof can be positioned such that the applied electric field radiates throughout the target tissue region, including, for example, where the electric field radiates outwardly and in a plurality of directions radially through the target tissue. In certain embodiments, the energy applied to the target tissue region can be selected such that electrically generated heat is minimized and elevations in tissue temperature can be avoided. For example, the applied electric field is can include a low-intensity (e.g., less than about 50 V/cm) and moderate frequency (e.g., between about 50 kHz and 300 kHz) alternating current field sufficient to provide low-power or non-thermal ablation of target cells. The electrode positioning and application of the electric field (e.g., low-power/non-thermal ablative electric field) of the present invention has demonstrated to be surprisingly effective in ablating cancerous cells can occur without a thermal effect being a factor in the ablation process. Moreover, the ablative process according to one embodiment of the present invention primarily occurs among abnormally proliferating cells or cells exhibiting unregulated growth (e.g., cancerous cells). Thus, the present invention provides the additional advantage of providing minimally invasive, selective ablation or destruction of cancerous cells, while leaving normal cells or tissue substantially intact.

Thus, in one aspect, the present invention includes improved ablation probes and related systems and methods. Ablation probes of the present invention can include electrodes deployable from positioning tubes or microcatheters, where the microcatheters are positionable in and advanceable from the ablation probe. Probes provide a sort of "multiphase" type of electrode deployment and positioning where positioning includes one phase with a microcatheter is deployed from the ablation probe, e.g., a distal portion of a delivery member, for initial aiming, and a second phase where an electrode is deployed from the microcatheter for further positioning of the electrode. The described micro-tube/catheter and electrode deployment configuration can provide more versatility and improved functionality in positioning of electrodes and can permit a wide range of motion and positioning of an electrode in a tissue. The probe configurations described herein were found to be particularly well suited, for example, for positioning of outer electrodes (e.g., secondary electrodes) that define an ablation volume. In addition to providing advantages with respect to improved electrode placement in a tissue and positioning, ablation probes described herein are useful in a wide variety of tissue ablation applications, including, e.g., both non-thermal and thermal (e.g., thermal RF ablation, microwave ablation, high voltage electroporation, etc.) types of tissue ablation.

The present invention includes methods of delivering an electric field to a target tissue. Such a method can include advancing an ablation probe into a patient; deploying a guide from the delivery member along a guide tissue penetration path, the guide path curving in a first direction; deploying an electrode from the guide along an electrode tissue penetration path, the electrode path curving in a second direction; and establishing current flow extending radially within the target tissue using the deployed electrode.

The present invention further includes devices for delivering an electric field to a tissue to destroy cells. A device can include a probe having a plurality of electrodes positionable in a target tissue region to at least partially define a treatment volume, the probe including a delivery member and a plurality of microtubes deployable from the delivery member, each of the electrodes being deployable from an associated one of the microtubes so that the electrodes will induce electric fields extending radially through the volume.

In yet another aspect, the present invention includes a system for tissue ablation. A system includes a probe including a delivery member, a plurality of microtubes deployable from the delivery member, and a plurality of electrodes deployable from the microtubes, the microtubes and electrodes defining a treatment volume when deployed. A system can further include an energy source coupled to the probe to establish a target tissue ablating current flow extending radially through the volume.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 1 illustrates a device according to an embodiment of the present invention.

FIGS. 15A and 15B show a cross-sectional, front view and side view, respectively, of a probe including microcatheters with deployable electrodes. FIGS. 15C and 15D show a first phase and a second phase of deployment, respectively.

DETAILED DESCRIPTION OF THE INVENTION

Figure 2C:
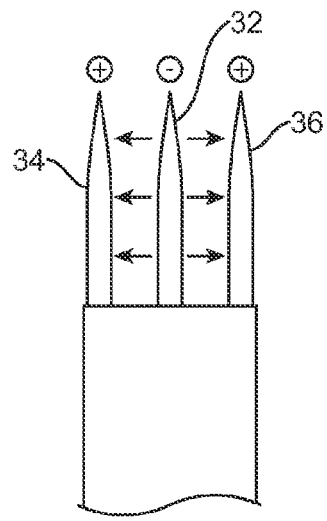
FIGS. 2A through 2C illustrate a device according to another embodiment of the present invention.

The present invention provides systems and devices, and related methods for low-power or non-thermal tissue ablation. According to the present invention, an electrode or plurality of electrodes can be introduced into a target tissue region and an electric field applied to the target tissue region. The energy applied to the target tissue region can be selected such that electrically generated heat is minimized and rises in tissue temperature can be avoided, thereby providing low-power or non-thermal ablation of target cells. Devices and methods of the present invention have been demonstrated to be effective in ablating cancerous cells without a thermal effect being a factor in the ablation process, with ablation occurring primarily among abnormally proliferating cells or cells exhibiting unregulated growth (e.g., cancerous cells). Thus, the present invention is advantageous in providing minimally invasive, selective ablation or destruction of cancerous cells, while leaving normal cells or tissue substantially intact.

In one embodiment, the target tissue region includes a mass or solid portion of tissue. Typically, the target tissue region includes cancerous cells including, for example, a target tissue region including a solid tumor. The volume of the tissue to be subject to the inventive methods can vary, and will depend at least partially based on the size of the mass of cancerous cells. Peripheral dimensions of the target tissue region can be regular (e.g., spherical, oval, etc.), or can be irregular. The target tissue region can be identified and/or characterized using conventional imaging methods and various imaging systems can be used for locating and/or positioning of a device or electrodes of the invention within a patient's tissue or at or within a target tissue region.

Electrodes can be positioned as described and an alternating electric field applied. Ablation techniques according to the present invention can be accomplished in some embodiments without an increase in local tissue temperature and without thermal effects of energy application being a primary means by which tissue ablation occurs. The applied electric field can include a low-intensity, moderate frequency alternating current. In some embodiments, electrode configuration and field application can take advantage of tumor physiology, including, orientation of dividing/proliferating cells within a target tissue region, and ensure that the electric field provided is substantially aligned with a division axis of a dividing cancerous cell.

Referring to FIG. 1, a device according to an embodiment of the present invention is described. The device 10 includes a delivery member 12 having a distal portion 14 and a proximal portion 16. The device 10 further includes a proximal portion 18 of the device that can be coupled (e.g., removably coupled) to the delivery member 12. Additionally, the device 10 can include conductive cables 20 electrically coupled to an energy source (not shown). The device includes a plurality of electrodes 22 at the distal portion 14 of the delivery member 12. The electrodes 22 can be positioned or fixed, for example, at the distal end of the delivery member 12 or positionable and deployable from a lumen of the delivery member 12 and retractable in and out of the distal end of the delivery member 12. The electrodes 22 can include a non-deployed state, where the electrodes 22 can be positioned within a lumen of the delivery member 12, and a deployed state when advanced from the distal end of the delivery member 12. Electrodes 22 are advanced out the distal end and distended into a deployed state substantially defining an ablation volume.

The present invention can include a variety of electrode compositions, configurations, geometries, etc, in certain embodiments, electrodes can include tissue-penetrating electrodes including, for example, small diameter metal wires having tissue-piercing or sharpened distal ends that can penetrate tissue as they are advanced within the target tissue region. Electrodes can be non-insulated or can include an insulated portion. In one embodiment, a non-insulated portion of the electrode provides an electric field delivery surface for delivery of electrical current to the surrounding tissue. Electrodes can be substantially rigid, e.g., so as to be more easily advanced through tissue, including hardened or more dense tissue, or can be more flexible, depending upon the desired use. In one embodiment, an electrode includes a needle or needle-like electrode or electrode having a substantially linear portion. In another embodiment, electrodes can be curved, having a curved portion or portion with a radius of curvature. Electrode composition can vary and in certain embodiments can include a memory metal (e.g., commercially available memory metals, Nitinol™, etc.) or sprung steel. Suitable electrode materials can include, e.g., stainless steel, platinum, gold, silver, copper and other electrically conductive materials, metals, polymers, etc. In certain embodiments, electrodes can be positioned in and deployable from a lumen of a catheter and/or microcatheter or other member for introducing the electrode into a tissue.

In another embodiment, the present invention can make use of one or more sensor mechanisms to provide feedback and/or control the ablation process. Sensor mechanisms can include sensors or detectors that detect and measure parameters such as temperature, current, voltage, impedance and the like. Certain embodiments of the present invention can include modifying the applied electric current at least partially based on a detected characteristic or a change in a detected characteristic. In one embodiment, for example, modification of the applied electric current can occur in response to a measured temperature, impedance, and the like. Modification can include, for example, modifying the voltage, frequency, etc. of the applied current and/or discontinuing application of the electric current, for example, where the ablation process or a stage thereof is determined to be completed.

A target tissue region can be located anywhere in the body where the tissue ablation methods of the present invention would be desired or beneficial. Target tissue is not limited to any particular type and non-limiting examples can include, e.g., breast tissue, prostate tissue, liver, lung, brain tissue, muscle, lymphatic, pancreatic tissue, and the like. The target tissue region will typically include a mass or solid portion of tissue. Typically, the target tissue region includes cancerous cells including, for example, a target tissue region including a solid tumor. The term "cancerous cell", as used herein, generally refers to any cells that exhibit, or are predisposed to exhibiting, unregulated growth, including, for example, a neoplastic cell such as a premalignant cell or a cancer cell (e.g. carcinoma cell or sarcoma cell), and are amenable to the ablation methods described herein. The volume of the tissue to be subject to the inventive methods can vary depending, for example, on the size and/or shape of the mass of cancerous cells, as well as other factors. Peripheral dimensions of the target tissue region can be regular (e.g., spherical, oval, etc.), or can be irregular.

Imaging systems and devices can be included in the methods and systems of the present invention. For example, the target tissue region can be identified and/or characterized using conventional imaging methods such as ultrasound, computed tomography (CT) scanning, X-ray imaging, nuclear imaging, magnetic resonance imaging (MRI), electromagnetic imaging, and the like. In some embodiments, characteristics of the tumor, including those identified using imaging methods, can also be used in selecting ablation parameters, such as energy application as well as the shape and/or geometry of the electrodes. Additionally, these or other known imaging systems can be used for positioning and placement of the devices and/or electrodes in a patient's tissues.

As set forth above, the electrode is positioned within the target tissue region and the applied electric field is sufficient to provide low-power or non-thermal ablation of target cells. The term "non-thermal ablation" as used herein generally refers to techniques of the present invention including the removal of or destruction of the function of tissue or cells of a tissue by application of an electric field, and where the energy application/delivery process occurs without a substantial increase in local tissue temperature and without thermal effects of energy application being a significant or primary means by which tissue ablation occurs. In many embodiments, an increase in local tissue temperature can be avoided altogether, with no resulting increase in temperature being detectable in the target tissue region. In some embodiments, however, small changes/elevations in temperature in the target tissue region may occur, but will typically be no more than a few degrees C. above body temperature (e.g., less than about 5 degrees C., but typically no more than about 2 degrees above body temperature), and without the thermal effects being the primary means by which tissue ablation occurs (e.g., no significant thermally-mediated, lethal protein denaturation). Typically, the applied electric field includes a low-intensity, moderate frequency alternating current. The moderate frequency employed according to the present invention, for example, will be less than that typically required for frictional/resistance heating to tissue surrounding the electrode (e.g., less than about 400 kHz, preferably about 300 kHz or less). In one embodiment, for example, the electric current provides a voltage field less than about 50V/cm. In another embodiment, the electrical current includes a frequency between about 50 kHz and about 300 kHz.

The voltage field and/or the frequency of the applied current can be held constant during energy application or varied. One or more treatment phases can be applied, with each phase having selected treatment parameters (e.g., energy parameters, duration, etc.). In some embodiments, providing a non-constant or varying voltage and/or frequency by "scanning" across a given range may be desired, for example, to ensure that the optimal ablative voltage/frequency is applied to the target tissue region. In another embodiment, a particular voltage and/or frequency can be selected prior to energy application. Furthermore, the electrode(s) can be positioned within the target tissue region such that electrical current application occurs from within the target tissue, and the target tissue is ablated from the inside out. In one embodiment, electrode(s) are positioned within the target tissue region (e.g., tumor) and the applied electrical current provides an electric field extending radially outward from the electrode. In certain embodiments, such positioning can take advantage of tumor physiology, including, e.g., orientation of dividing/proliferating cells within a target tissue region, and ensure that the electric field provided by the electrode is substantially aligned with a division axis of a dividing cancerous cell.

Figure 2A:
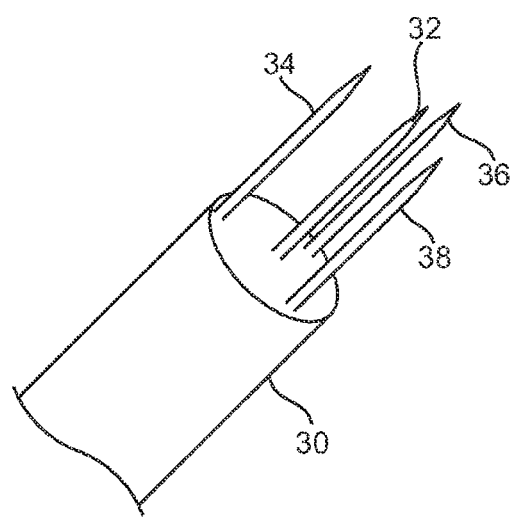
Figure 2B:
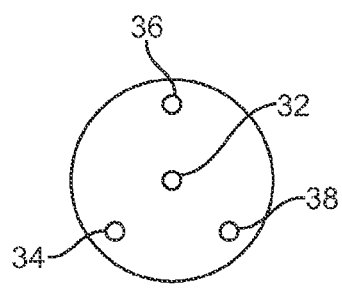

FIGS. 2A through 2C show a device having a plurality of electrodes according to another embodiment of the present invention. As shown, the device 30 includes a plurality of electrodes extending from the distal portion of the device. FIG. 2A shows a three dimensional side view of the device having the plurality of electrodes. FIG. 2B shows a top view of the device illustrating the electrode arrangement. The plurality includes a centrally positioned electrode 32 and outer electrodes 31, 36, 38 spaced laterally from the central electrode 32. The illustrated electrodes include substantially linear needle-like portions or needle electrodes. The electrodes extend from the distal portion of the device and are oriented to be substantially parallel with the longitudinal axis of the device 30. Additionally, each electrode is substantially parallel with other electrodes of the plurality. The plurality of electrodes substantially define the ablation volume, with the outer electrodes 34, 36, 38 substantially defining a periphery of the ablation volume and the electrode 32 positioned within or at about the center point of the defined periphery. Each of the electrodes can play different roles in the ablation process. For example, there can be changes in polarity and/or polarity shifting between the different electrodes of the device. As with other devices of the invention, electrodes can be electrically independent and separately addressable electrically, or two or more electrodes can be electrically connected, for example, to effectively function as one unit. In one embodiment, for example, outer electrodes 34, 36, 38 can be electrically connected and, in operation, include a polarity different from that of the inner electrode 32. As illustrated in FIG. 2C the electrodes 32 and 34, 36 of the device can include opposing charges (e.g., bipolar). In such an instance, the applied electrical current can provide an electrical field, as illustrated by the arrows, extending radially outward from the central electrode 32 and toward the peripherally positioned or outer electrode(s) 34, 36.

In some embodiments, devices and/or systems of the present invention include electrically floating systems or systems designed to operate without an earth grounding. In some instances, it was observed that electrode configurations that were electrically floating in this manner allowed more accurate or controllable field application and/or delivery. The low-power requirements of systems according to certain embodiments allow more design options in configuring devices and systems that are electrically floating, as described, compared, for example, to known techniques such as thermal RF or microwave ablation, or high-voltage irreversible electroporation that require much higher powered energy delivery and corresponding power sources.

Figure 3A:
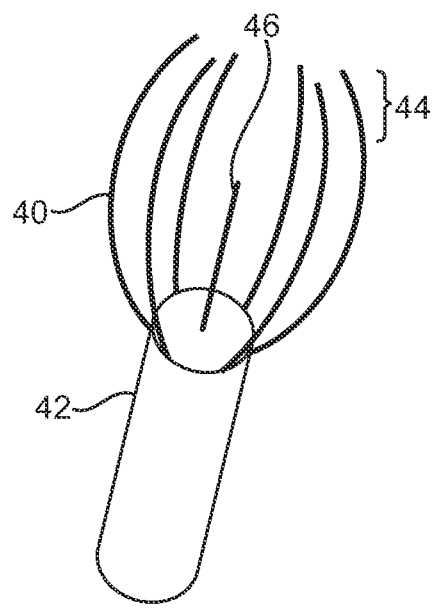
FIGS. 3A and 3B show a device having an electrode configuration according to an embodiment of the present invention.
Figure 3B:
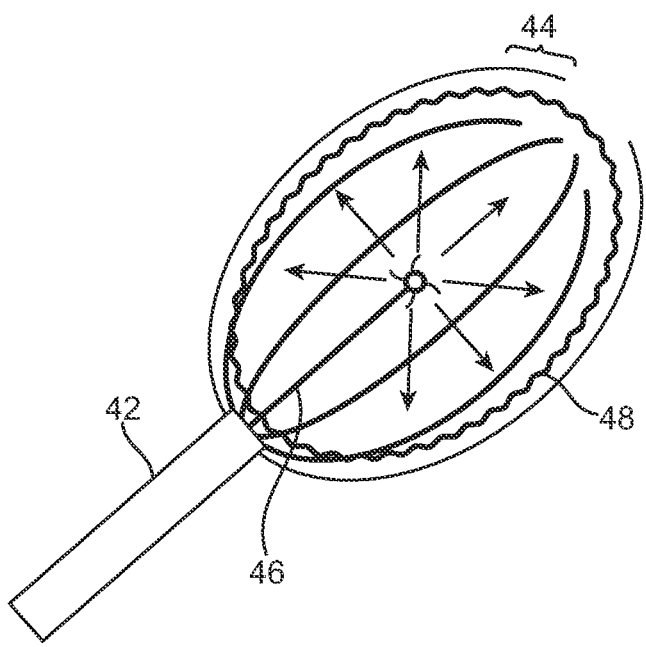

Another embodiment of a device of the invention is described with reference to FIGS. 3A and 3B. The device 40 includes a plurality of electrodes at or extending from the distal end 42 of the device 40. The plurality of electrodes includes outer positioned electrodes 44 that are curved and substantially define an ablation volume. An electrode 46 is positioned within the volume defined by the outer electrodes 44 and spaced from the electrodes 44. The central electrode 46 is shown as being substantially linear and parallel with the longitudinal axis of the device 40, although other configurations will be available, FIG. 3B shows a target tissue 48 within the periphery defined by the outer electrodes 44 with an electrical current being applied to the target tissue 48, and illustrating an oblong or oval ablation volume being defined by the curved electrodes 44. Thus, a target tissue region 48, such as a solid tumor, can essentially be encased within the volume defined by the outer electrodes 44. Arrows illustrate an electric field extending outward and radially from the electrode 46 and in a plurality of different directions.

Figure 4:
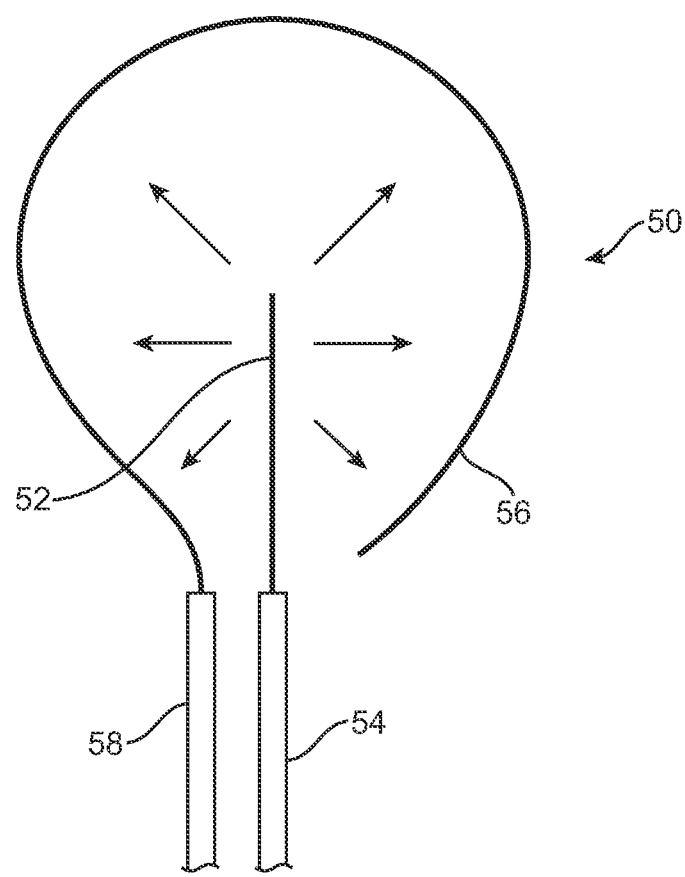
FIG. 4 illustrates an electrode arrangement according to an embodiment of the present invention.

Electrodes of a device according to another embodiment of the present invention are described with reference to FIG. 4. The device 50 includes a substantially linear electrode 52 that is retractable in and out of a microcatheter 54 and an electrode 56 having a curved portion, the electrode retractable in and out of a microcatheter 58. Microcatheters 58 and 54 can be included in a single delivery member, such as in a lumen(s) of a delivery catheter or can be independently arranged, e.g., for individually accessing and addressing a target tissue. One outer electrode is illustrated (e.g., electrode 56), though multiple outer or secondary electrodes can be provided, as illustrated in other embodiments (e.g., see below).

Figure 5A:
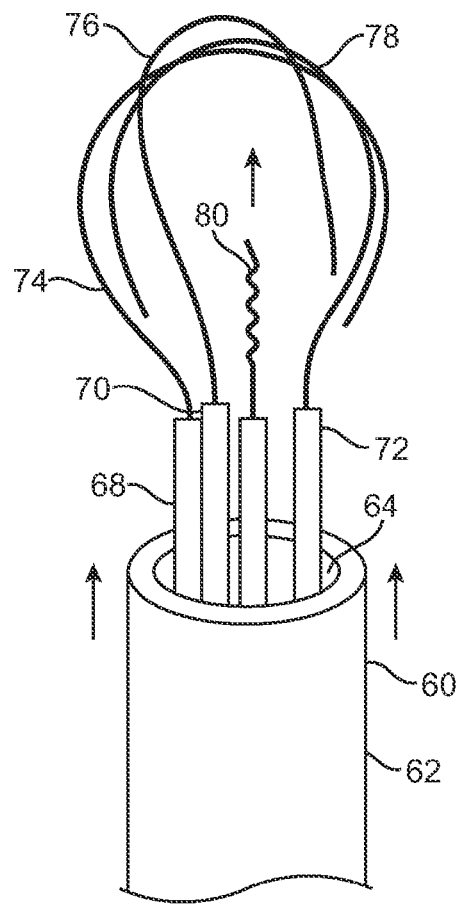
FIGS. 5A and 5B illustrate a catheter and microcatheter device according to another embodiment of the present invention.
Figure 5B:
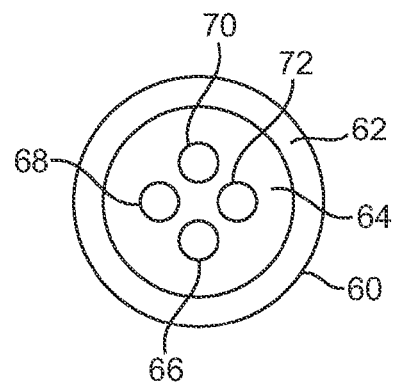

A device can include a plurality of electrodes, each deployable or retractable in and out of a microcatheter, with each microcatheter/electrode assembly optionally positioned within a central lumen of a larger delivery member, as illustrated in FIGS. 5A and 5B. The device 60 includes a delivery member 62 with a lumen 64, and microcatheters 66, 68, 70, 72 positioned in the lumen. FIG. 5B shows a top view of the device with microcatheters 60, 68, 70, 72 positioned in the lumen 62 of the delivery member 60. Electrodes 74, 76, 78 each having a curved portion, are deployable from microcatheters 68, 70, 72 and, in a deployed state, substantially define an ablation volume. Electrode 80 is deployable from microcatheter 66 is positioned within the ablation volume substantially defined by electrodes 74, 76, 78.

Figure 6A:
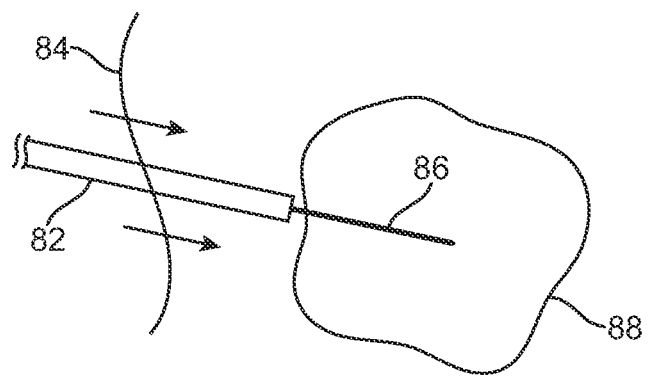
FIGS. 6A and 6B illustrate a method according to an embodiment of the present invention.
Figure 6B:
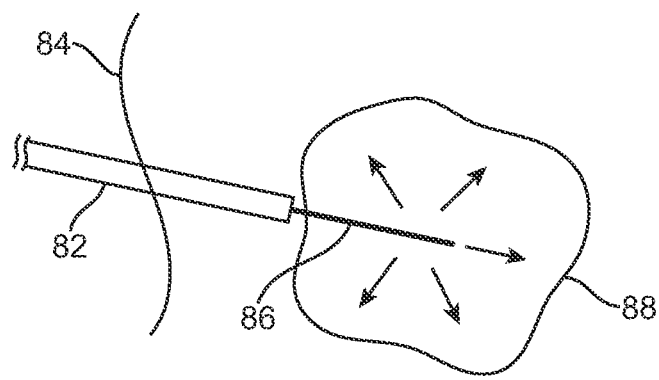
Figure 7A:
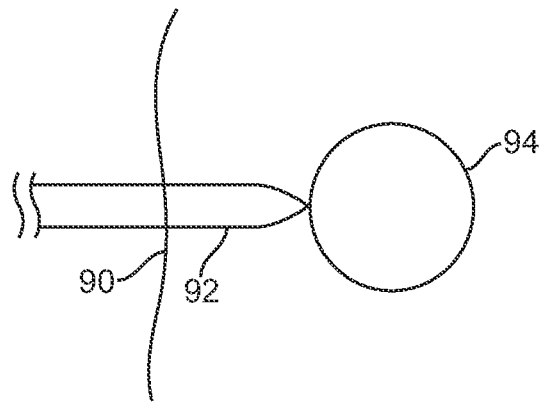
FIGS. 7A and 7B illustrate a method according to another embodiment of the present invention.
Figure 7B:
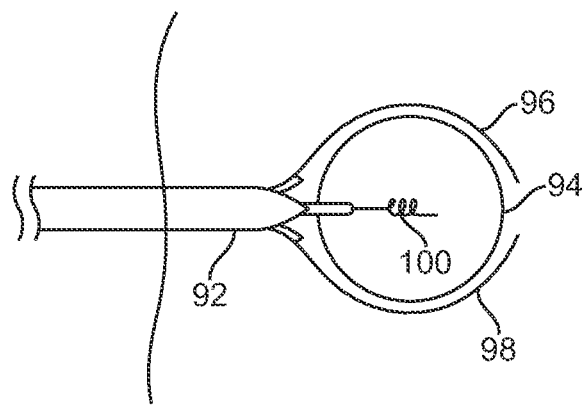

In use, as shown in FIG. 6, a device 82 of the present invention can be advanced through the patient's tissue 84, and an electrode 86 of the device 82 positioned within a target tissue region 88 tumor). Once the electrode is positioned in the target tissue region 88, electrical current is delivered to the target tissue region 88. As the electrode 86 is positioned within the target tissue region 88, the applied electrical current can provide an electric field that radiates outward and in a plurality of directions. A system or device of the invention can be operated in monopolar mode or bipolar mode. In one monopolar operation embodiment, a second electrode can be placed, for example, outside the patient's body, such as by positioning the patient on a conductive pad or plate (e.g., metal plate) and may make use of conductive materials, such as conductive gels or adhesives, placed between the patient's skin and the second electrode. In a bipolar mode embodiment, outer electrodes substantially defining an ablation volume can function as return electrodes, or complete a circuit with an electrode(s) positioned within the ablation volume, with applied current flowing through tissue of the target region positioned between the outer electrodes and electrode(s) positioned within the ablation volume. FIG. 7 shows use of a device of the present invention according to another embodiment of the present invention. As described above, the device 90 is advanced through the patient's tissue and the delivery member 92 positioned proximate to the target tissue region 94. Once the delivery member 92 is positioned, a plurality of electrodes 96, 98, 100 can be deployed from the delivery member 92. Outer electrodes 96, 98 are deployed at or around the perimeter of the target tissue region 94, e.g., at about the margin of the target tissue region (e.g., tumor margin) and substantially define the ablation volume or target region. The inner electrode 100 is positioned within the ablation volume.

The present invention can include various means of accessing or addressing a target tissue and positioning electrodes/probes for delivery of the described ablative treatment. Typically, positioning of a device of the invention will include a minimally invasive access and positioning techniques, including, e.g., access techniques commonly used with other types of tissue ablation (e.g., thermal RF ablation, microwave ablation, high-voltage electroporation, and the like). For example, devices of the invention can be introduced percutaneously through the skin and advanced through tissue and positioned at a target tissue. Though, addressing a target tissue and positioning of a device can occur in conjunction with more conventional surgical techniques.

Figure 8A:
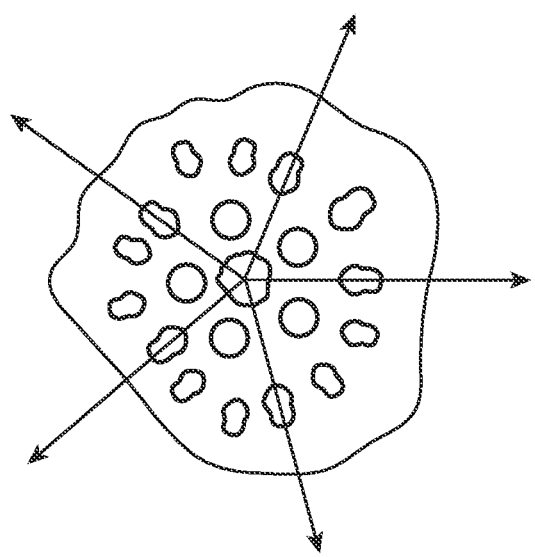
FIGS. 8A and 8B illustrate a tumor or mass of cancerous cells, with FIG. 8B showing a focused view of a dividing cancerous cell.
Figure 8B:
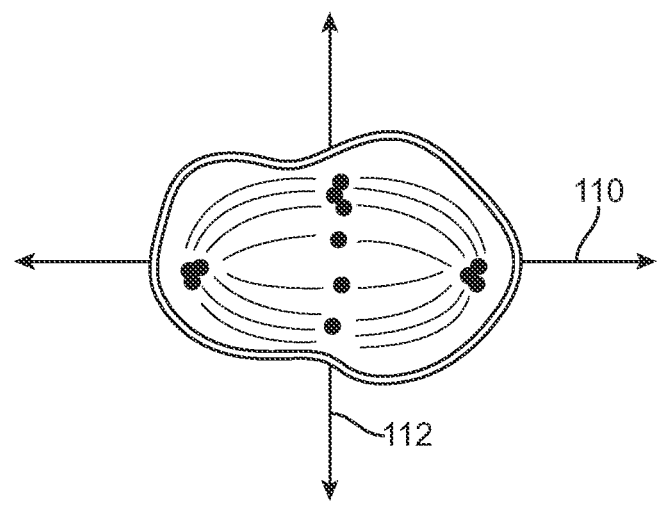

As set forth above, certain embodiments of the present invention include positioning of an electrode within the target tissue region and applying an alternating electrical current, with the applied electrical current providing an electrical field that radiates outwardly from the positioned electrode. Electric field application in this manner was found to be highly effective in disrupting and destroying cancerous cells via low-power ablation and in the absence of a thermal ablative effect. In certain embodiments, disruption of cancerous cells and resulting ablation according to the present invention even more effectively occurred where the electrical field provided by an electrode of an inventive device was substantially aligned with a division axis of a dividing cancerous cell or plurality of cells. FIG. 8A shows a simplified version of a growth pattern and physiology of a cancer tumor or solid mass of cancerous cells, illustrating tumor growth by cancer cells dividing outwardly from the center of a region. Arrows indicate division axes of cancerous cells dividing outwardly from the center. FIG. 8B shows a focused and simplified view of a dividing cell of the tumor of FIG. 8A, further illustrating the concept of an axis of cell division. The illustrated dividing or proliferating cancerous cell (illustrated at a metaphase stage of mitosis) includes an axis of cell division 110 substantially orthogonal to a metaphase plate axis 112, where the cell divides substantially along the plate axis 112 and cell proliferation and growth occurs along the cell division axis 110. Thus, in certain embodiments of the invention, the positioning of an electrode within a tissue region, e.g., proximate to the center region of a tumor or mass of cancer cells, and/or the configuration and arrangement of the electrodes of the device, can be selected such that the electrical field radiates outwardly from about the center region and the electric field is substantially aligned with the division axes of cells of the growing tumor.

Furthermore, the electric field application as described was observed to be particularly effective in selectively disrupting and destroying the dividing cancerous cells, while having little or no effect on normal cells that were not exhibiting unregulated growth and proliferation. Without being bound by any particular theory, electric field application as described may specifically disrupt the cell division process (e.g., mitosis) or progression through the cell cycle, or a stage or process thereof (e.g., mitotic spindle formation, microtubule polymerization, cytoplasmatic organelle function or arrangement, cytokinesis, cellular osmotic balance or the like) and, therefore, more particularly effects cells exhibiting unregulated growth (e.g., cancerous cells) and progressing more rapidly through the cell cycle.

According to the present invention, a target tissue region can be ablated in whole or in part. It will be recognized that while it is generally desirable to ablate as much of the target region or tumor as possible, in some embodiments, methods can include ablation of a portion or less than the entirety of the target region. In some instances, partial tumor ablation can be sufficient to ultimately destroy or kill an entire tumor or cancerous tissue region.

Figure 9A:
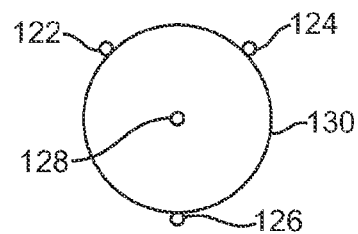
FIGS. 9A through 9D show a device and method according to an embodiment of the present invention.
Figure 9B:
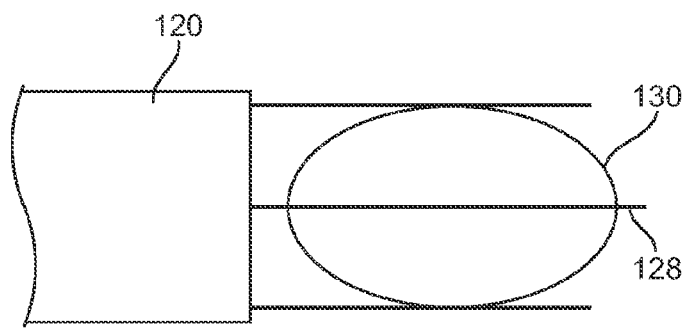
Figure 9C:
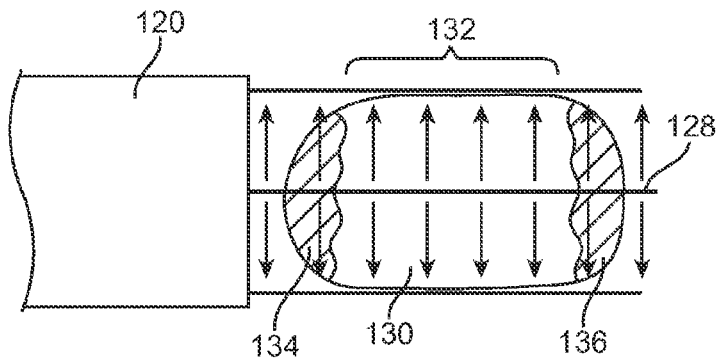
Figure 9D:
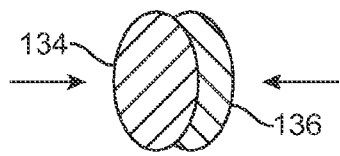

Use of a device according to an embodiment of the invention (e.g., the device of FIG. 2A through 2C) is discussed with reference to FIGS. 9A through 9D. The device 120 includes a plurality of electrodes, including outer electrodes 122, 124, 126 substantially defining an ablation volume and at least one inner electrode 128. The device can be positioned at a target tissue region including a tumor or portion thereof. The tumor 130 is shown positioned substantially within the ablation volume, with the inner electrode 128 positioned about through the center of the tumor and outer electrodes 122, 124, 126 spaced laterally from the inner electrode 128 and positioned at about or slightly outside the tumor margin. FIG. 9A shows a top sectional view of the tumor 130 and positioned electrodes 122, 124, 126, 128, and FIG. 9B shows a side view of the same. An electric field, illustrated by the arrows in FIG. 9C, is provided by the positioned electrodes and the application of an electrical current. As can be seen, in the parallel straight needle electrode configuration shown in FIGS. 9A through 9C, the electrical field along the length of the ablation volume is oriented in a direction orthogonal to the longitudinal axis of the device. The electric current emanating from the center electrode 128 toward the outer electrodes 122, 124, 126 provides a field that is substantially aligned with the direction of cell division for many of the tumor cells, particularly those in region 132, which divide in a direction from the tumor center and outward (see, e.g., FIGS. 8A and 8B). It will be recognized that arrows are provided for illustrative purposes, and that embodiments of the invention are not limited to any particular current and/or electrical field direction, but may include directions other than and/or in addition to those specifically illustrated. The tumor includes region 132 where direction of tumor cell division is believed more closely aligned with the electrical field. In the illustrated configuration, the tumor can include regions 134, 136 at opposing ends of the tumor that may include a greater proportion of cells having cell division axes not in alignment with the provided electric field, or, in other words, are at an angle relative to the electric field and may remain alive following application of energy, while a greater proportion of cells of region 132 are ablated. However, in one example, using tumor ablation in this manner, the tissue/cells of region 132 were ablated and materials subsequently removed from the treatment site (e.g., squeezed out by application of pressure) and/or absorbed by surrounding tissue, and regions 134 and 136 were observed to collapse inward forming a flat, "pancake-like" tissue residue (FIG. 9D), which eventually died subsequent to energy application. Remarkably, numerous experimental (e.g., animal) models that were subject to the described ablation techniques of the present invention demonstrated complete remission of detectable tumor. These results indicated that the present inventive methods effectively ablate tumor tissue, can destroy a solid tumor, even where less than the entirety of tumor tissue is ablated, and illustrated the improved tissue ablation where the electric field is aligned with the direction of cell division of cancerous cells.

Figure 10:
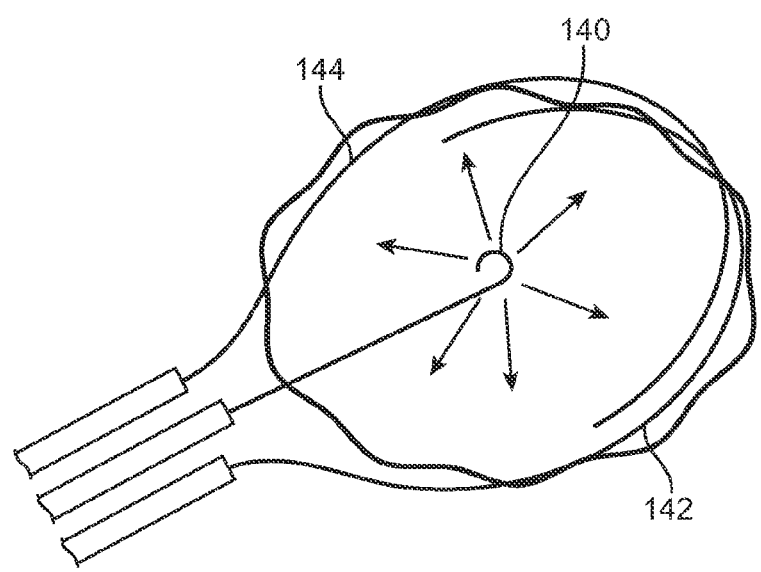
FIG. 10 shows a device according to an embodiment of the present invention.

Another embodiment of a device of the present invention is illustrated in FIG. 10. As discussed above, device configuration and electrode arrangement can be selected such that the electrical field radiates outwardly from about the center of the target tissue region and the electric field is substantially aligned with the division axes of certain cells of the growing tumor. More optimal application of electrical energy and alignment of the electric field with division axes of the growing tumor can be accomplished by both positioning of the electrodes in the target region and selected electrode configuration and/or geometry of the device. In one embodiment, for example, device can include an inner electrode 140 and a plurality of outer electrodes 142, 144 that are curved. The inner electrode 140 can additionally include a curved or non-linear distal portion. Having curvature on electrodes can help select an applied electric field that radiates in a plurality of directions, including directions other than orthogonal to the longitudinal axis of the device or inner electrode. The outer curved electrodes substantially define the ablation volume and the inner electrode is positioned within the ablation volume. Arrows illustrate the field emanating from the center in a plurality of directions and substantially in line with dividing cancerous cells of the target tissue region. In some instances, the electric field provided by this configuration may align with a greater portion of cancerous cells of the target tissue region compared, for example, to the straight needle electrode configuration illustrated in FIGS. 9A through 9D.

As the ablation process is initiated, the field intensity is highest at the inner or central electrode and within tissue around and in close proximity to the inner or central electrode. As the ablation process progresses, cancerous cells near the inner electrode are observed to be destroyed or ablated first. The ablated cells effectively "liquefy" or assume properties of a low impedance, liquid-like material. The term "liquefy" is used herein for convenience and illustrative purposes, and does not necessarily imply any particular mechanism of ablation or cell death, which may include cell blebbing, apoptosis, lysis, or some other cellular process, and/or some combination thereof. Another possible cause of cell destruction may include disruption of cellular membrane integrity, e.g., including dielectric breakdown of one or more cellular membranes (see, e.g., below). The liquid-like material surrounds the central electrode and effectively enlarges the higher field intensity ablative area, with the highest field intensity ablative area being at the outer perimeter of the liquid-like material. Thus, the liquid-like material is said to become a "virtual electrode". As the ablation process progresses, the outer perimeter of the liquid-like material or "virtual electrode" expands, essentially ablating the target tissue region from the inside out. In some embodiments, target tissue regions were observed to be more pliable and soft or mushy following the ablation process. The ablated, liquid-like tumor tissue was eventually removed from the treatment site and/or absorbed by the surrounding tissue, and no longer detectable.

Figure 11A:
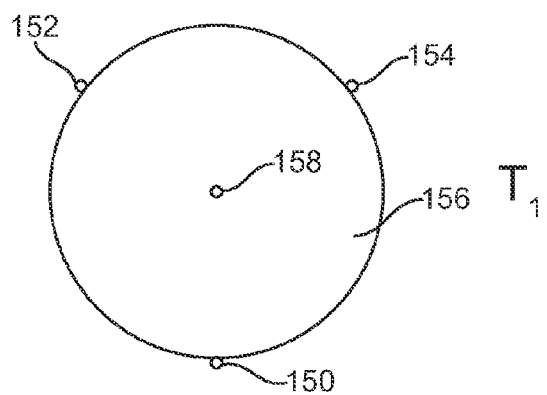
FIGS. 11A through 11C illustrate an ablation method according to an embodiment of the present invention.
Figure 11B:
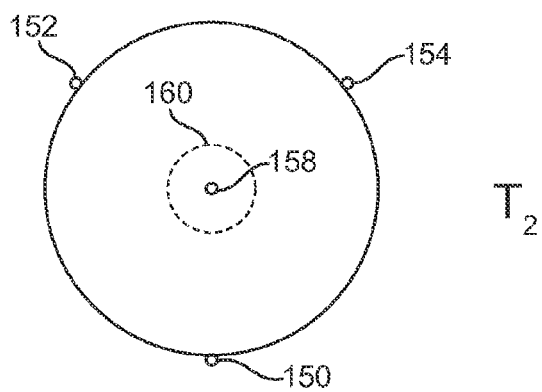
Figure 11C:
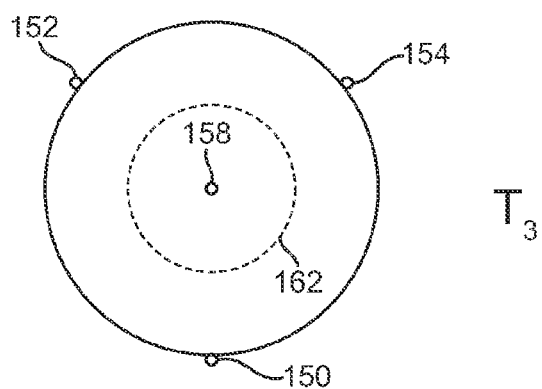

The virtual electrode effect is illustrated with reference to FIGS. 11A through 11C, showing a cross section view of electrodes positioned in a target tissue region. Outer electrodes 150, 152, 154 are positioned at about the margin or outer periphery of the tumor 156, and inner electrode 158 is positioned at about a center point of the volume defined by the outer electrodes 150, 152, 154. Ablation is shown at T1, or the beginning of the ablation process (FIG. 11A); T2 after ablation has begun with the expanding liquid-like tissue region 160 (FIG. 11B); and subsequent time T3, with the liquid-like tissue region 162 expanded further outward from the inner electrode 158 and toward the outer electrodes 150, 152, 154 (FIG. 11C).

The ablation process, including the progress thereof, can be monitored by detecting the associated change in impedance in the ablated tissue. Once the outer perimeter of the ablated, liquid-like tissue reaches the outer electrodes defining the ablation volume, the impedance stabilizes or levels out. Thus, the progress of the ablation process can be monitored by measuring change in impedance, and electric field application discontinued once a change in impedance is no longer observed.

Feedback measurements can also be used to ensure that the ablation of the target cancerous cells occurs by non-thermal ablation. In certain embodiments it may be desirable to generate as much field intensity at the inner electrode as possible without causing a hyper-thermal effect or thermal ablation. Certain hyper-thermal effects would be observable and distinguishable from the desired non-thermal ablation of the present invention, since thermal ablation would cause destruction of the surrounding cells without the "liquefying" effect described above. For example, if cell destruction is caused by a thermal ablation process, the impedance of the treated tissue may not decrease since the impedance of cells that are charred or become necrotic due to thermal effects typically increases. In one embodiment, non-thermal ablation according to the present invention can include placement of a sensor, such as a thermocouple, within the target tissue region (e.g., proximate to the inner electrode), and selection of an applied field intensity as below the intensity that would cause thermal effects on the target cells.

Figure 12A:
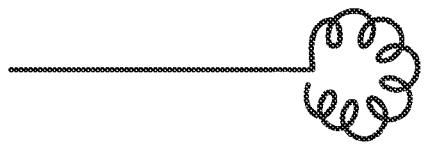
FIGS. 12A through 12F illustrate exemplary electrodes according to various embodiments of the present invention.
Figure 12B:
Figure 12C:
Figure 12D:
Figure 12E:
Figure 12F:

As stated above, in some instances, it may be desirable to increase the field intensity emanating from the position of the inner electrode within the target tissue region. In one embodiment of the present invention, field intensity can be increased by increasing the surface area of the inner electrode that is placed within the target tissue region. Various embodiments of increased surface area electrodes are illustrated in FIGS. 12A through 12F, though other configurations will be available. In one embodiment, the electrode includes a coiled distal portion that can further form a circular pattern (FIG. 12A), a corkscrew (FIG. 12B), or a simple coil (FIG. 12C). In another embodiment, a small wire mesh could be included at the electrode distal end, and expanded when placed within a target tissue region (FIG. 12D). In other embodiment, an electrode can include a "Litz" wire-type of electrode, where the distal end includes a plurality of small wires expanded in an array (FIG. 12E). In another embodiment, the distal portion can include a shape resembling two cones stacked base to base, or from a side view having a diamond shape (FIG. 12F). The pointed opposing distal and proximal portions of the double cone/diamond end can facilitate insertion and retraction of the electrode in tissue. Numerous other configurations are available and can include, for example, a ring, sphere, corkscrew, helix, concentric helixes, or plurality thereof, array of needles, length of non-resilient, string-like wire that is pushed out a tube and forms a small ball of wire similar to a string piling up randomly in a small container, and the like.

Figure 13A:
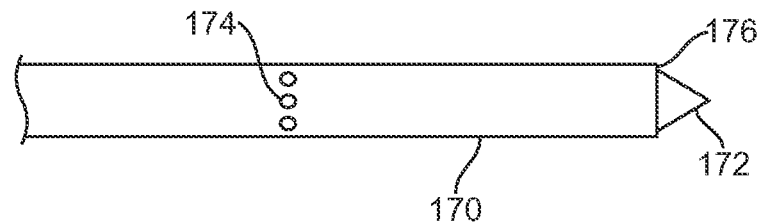
FIGS. 13A and 13B illustrate a device according to embodiment of the present invention.
Figure 13B:
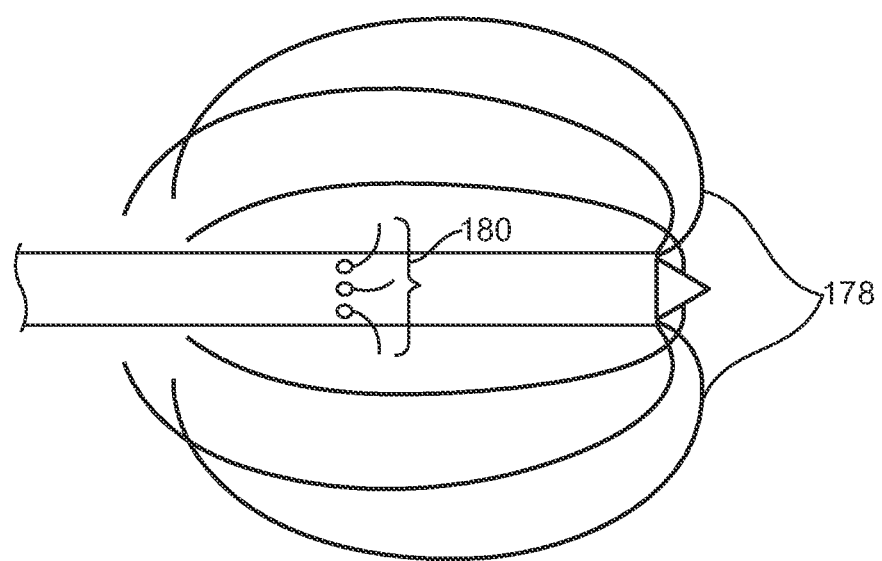

Another embodiment of a device of the present invention is shown in FIG. 13. The device includes a delivery member 170 with a tissue piercing distal portion 172. The delivery member includes a lumen and openings 174 on the body and at 176 the distal end. A plurality of electrodes are positionable within the lumen of the member. In a deployed state, outer electrodes 178 extend out the openings 176 at the distal end of the member 170 and invert in an umbrella-like orientation. The deployed outer electrodes 178 substantially define an ablation volume. Electrodes 180 extending out the openings 174 of the body are spaced from the outer electrodes 178 and positioned within the ablation volume.

Figure 14A:
FIGS. 14A and 14B illustrate a device according to another embodiment of the present invention.
Figure 14B:
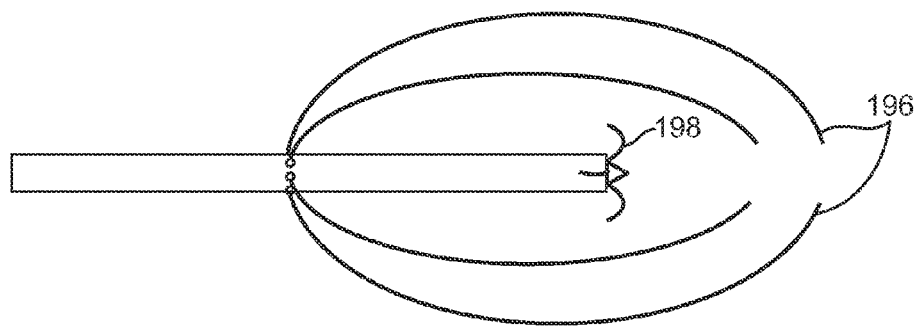

FIG. 14 illustrates a device similar to that shown in FIG. 13. Referring to FIG. 14, the device includes a delivery member 190 with a distal portion, openings 192 on the body and at the distal end 194. Outer electrodes 196 deploy distally out the body openings 192 and define a volume surrounding the electrodes 198 deployed and extending out the distal end opening 194.

As noted above, in some embodiments, electrodes can be deployable from small, electrode guides or positioning tubes, e.g., microtubes or microcatheters, positionable in and advanceable from a distal portion of an ablation probe. The terms catheter or microcatheter, as used herein, refer generally to an elongate tube having a lumen. For example, an ablation probe of the present invention can include a distal portion or a delivery member having a lumen with an electrode aiming/positioning microtubes/microcatheters positioned within the lumen of the delivery member, with electrodes disposed in the microcatheters and deployable therefrom. Both microcatheters and electrodes can include a shape memory metal and include a preformed shape for deployment. In use, the distal portion of the probe can be positioned proximate to a target tissue, for example, by advancing the probe through a patient's tissue. Once in position, a microcatheter can be deployed from the delivery member and can act as an initial advancement or guide tube as advanced or deployed from the delivery member for initial aiming and/or positioning of the electrode disposed therein. Following advancement and positioning of the microcatheter, the electrode can be deployed from the microcatheter for desired positioning of the electrode at or in the target tissue region. The described "multi-phase" type of microcathter/ electrode deployment configuration can provide more versatility and improved functionality in positioning of electrodes, and can permit a wider range of motion or positioning of an electrode in a tissue compared to other configurations, such as deployment of only an electrode alone. The described configuration was found to be well suited, for example, for positioning of outer electrodes (e.g., secondary electrodes) to define an ablation volume, particularly where electrodes are first advanced in a direction angling away from the delivery member and current flow center and then advanced in a direction that moves the electrode back toward the delivery member/center.

Figure 15A:
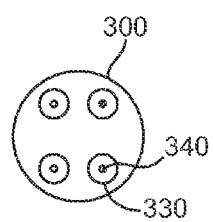
FIGS. 15A through 15D illustrates a device and ablation method according to an embodiment of the present invention.
Figure 15B:
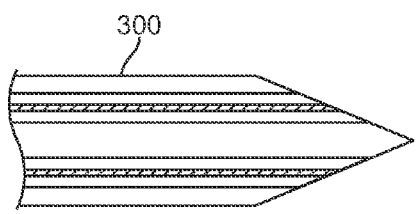
Figure 15C:
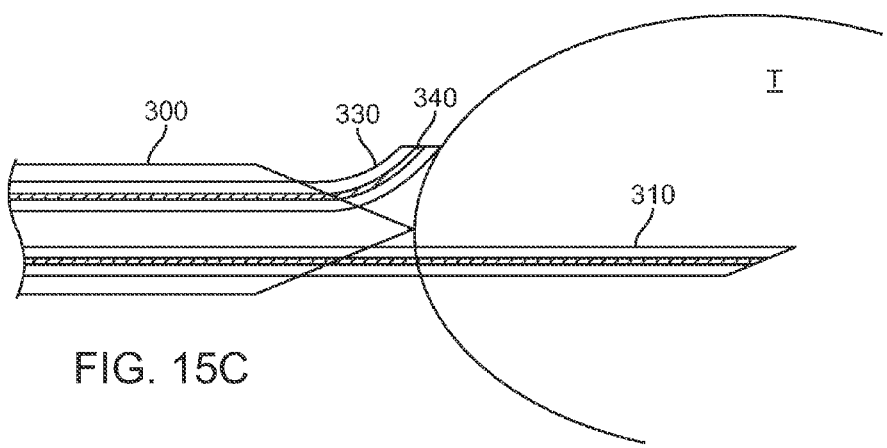
Figure 15D:
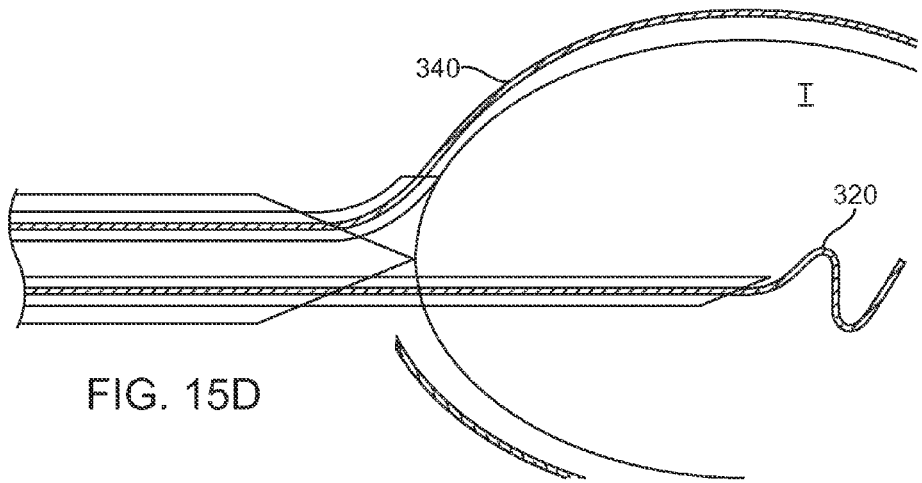

An embodiment of a device of the invention is described with reference to FIGS. 15A through 15D, the device illustrating an embodiment including electrodes deployable from microtubes or microcatheters. The device includes a plurality of electrodes positioned in a lumen of a delivery member 300 of a probe or delivery catheter, with each electrode positioned within a microcatheter as illustrated by microcatheter 330 and electrode 340, and each microcatheter positioned within the lumen of a delivery member 300. Microcatheters can act as guide tubes as advanced or deployed from delivery member 300 for initial aiming and/or positioning of electrodes contained therein (see below). FIG. 15A shows a cross-sectional front view of microcatheters positioned in the lumen of delivery member 300. The delivery member or probe 300 can include a tissue piercing end that is pointed or sharpened so as to more easily be inserted into the tissue of a patient, as illustrated in FIG. 15B. Similarly, a microcatheter (e.g., microcatheters 310, 330) can include a pointed or sharpened tissue piercing end. In use, the delivery member 300 can be advanced through the tissue of a patient and the distal end positioned proximate to a target tissue region (e.g., tumor "T") and the microcatheters are deployed from the delivery member for positioning of electrodes in a desired arrangement. As shown in phase 1 deployment (FIG. 15C), microcatheter 310 is advanced distally from the distal end of the delivery member and into the target tissue region, where the electrode 320 of the microcatheter can be deployed. Microcatheters can include shape memory metal (e.g., Nitinol) such that microcatheters assume a desired and/or predetermined shape when deployed from the delivery member 300, as illustrated with microcatheter 330. Thus, microcatheter 330 can also be deployed from the delivery member 300 to aim the electrode 340. In phase 2 deployment (FIG. 15D), electrode 340 is deployed in the direction aimed by microcatheter 330, such as around the outer perimeter of the target tissue region (e.g., tumor margin). Both microcatheters and electrodes positionable therein can be made of memory shape metal such as nitinol so as to assume a predetermined configuration when deployed. Other phases of use can further be included.

Figure 16:
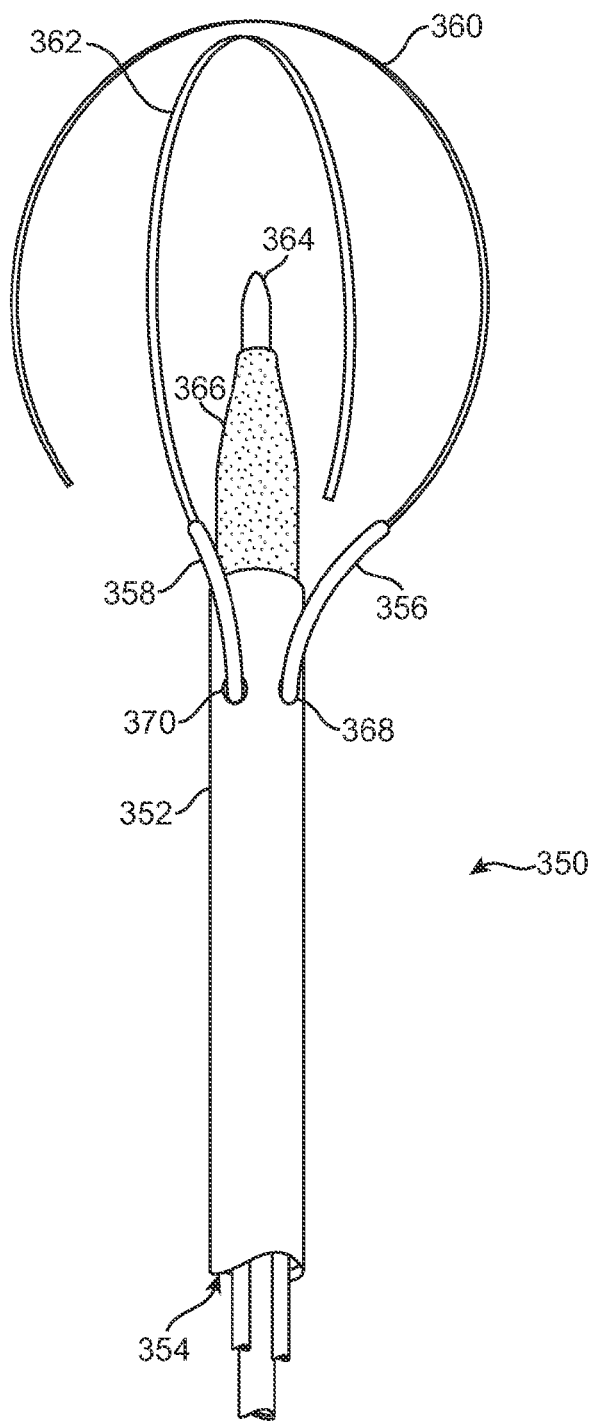
FIG. 16 illustrates a probe having deployable guide tubes and electrodes according to another embodiment of the present invention.

An ablation probe having deployable electrodes and microcatheters is described with reference to FIG. 16. The probe 350 includes a delivery member 352 that forms a distal portion of the probe 350, and includes lumen 354 in which microtubes/microcatheters 356, 358 can be positioned and deployed therefrom. The probe 350 is shown in a deployed state with microtubes 356, 358 advanced from lumen 354 of the delivery member 352 through openings 368, 370, respectively. Electrodes 360, 362 are shown advanced from microcatheters 356, 358, respectively. The deployed electrodes 360, 362 substantially define an ablation volume with an electrode 364 positioned within the ablation volume. The centrally positioned electrode 364 can be deployable from a delivery member as described above or can be substantially fixed or positioned in desired arrangement. As shown, the electrode 364 is positioned to form a distal tip of the probe and can be pointed or sharpened so as to more easily puncture through (e.g., percutaneously) and/or advance through a tissue. The probe can further include a tapered portion 366 (e.g., insulated portion) to facilitate advancement/positioning of the probe 350. The probe 350 is typically advanced to a target location with electrodes in a non-deployed state. Once the probe is positioned at a desired location, microcatheters 356, 358 can be advanced through openings 368, 370 the delivery member 352, e.g., for initial aiming of the electrodes in the desired direction and then electrodes 360, 362 deployed from the microcatheters 356, 358 for further positioning and formation of the ablation volume. Typically, the target tissue (e.g., cancerous tissue) will be at least partially contained in the ablation volume. Current can be applied through the electrodes of the probe such that an applied field radiates throughout the ablation volume, between the central electrode 364 and outer electrodes 360, 362, thereby applying a field in radially and in a plurality of different directions.

Figure 17A:
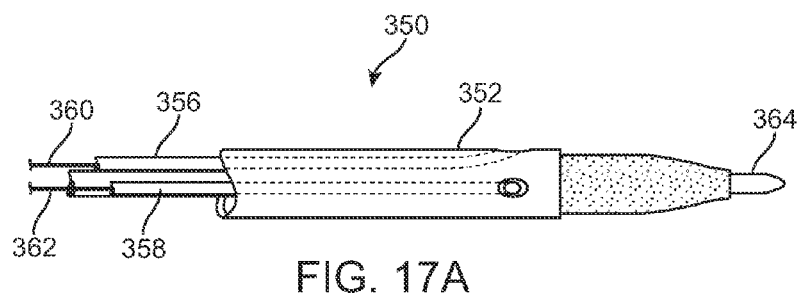
FIGS. 17A through 17C illustrate a probe according to an embodiment of the present invention and deployment of a guide tube and associated electrode.
Figure 17B:
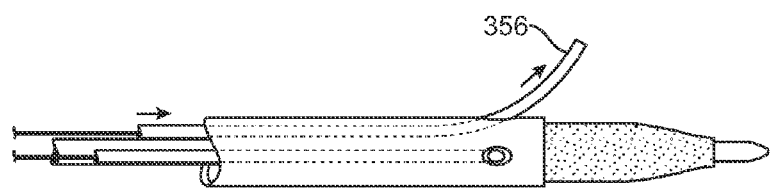
Figure 17C:
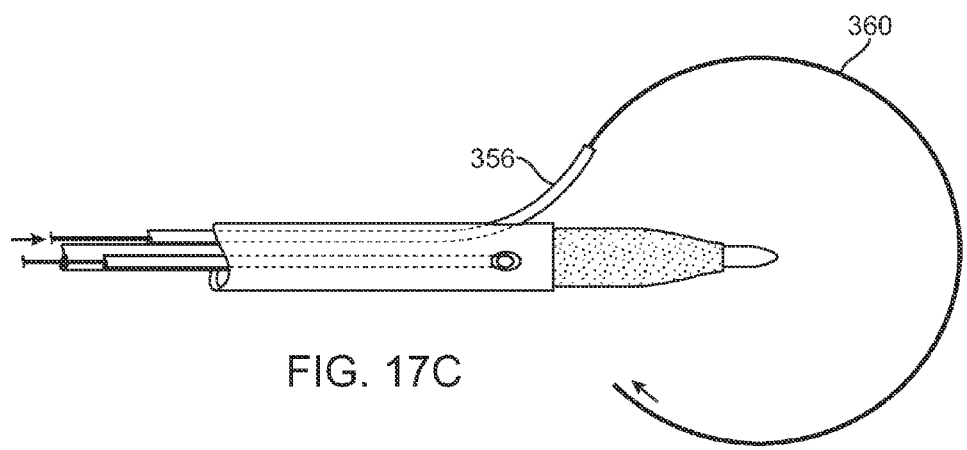

Phased deployment of components of a probe 350 are illustrated with reference to FIGS. 17A through 17C. As described above, the probe 350 includes a distal portion including a delivery member 352 having a lumen 354, and microcatheters 356, 358 with electrodes 360, 362 positioned therein. The probe 350 further includes distally positioned electrode 364. FIG. 17A illustrates probe 350 in anon-deployed state. Microcatheters are deployed from the delivery member, as illustrated in FIG. 17B with deployment of microcatheter 356. Deployment of a microcatheter 356 can include application of a force to a proximal portion of the microcatheter 356 so as to advance the distal portion of the microcatheter 356 from the delivery member 352 for deployment and initial positioning or aiming. Deploying the microcatheter 356 from the delivery member 352 guides the microcather 356 along a guide path (e.g., tissue penetration path) that can curve in a desired direction or at an angle. Following deployment of microcatheter 356, electrode 360 can be deployed from the microcatheter 356 for further positioning of the electrode 360, as illustrated in FIG. 17C. In this manner, the advancing the microcatheter 356 first guides deployment away from the current flow center, e.g., electrode 364, then deploying the electrode 360 curves the electrode 360 in a direction and along a path that advances the electrode 360 circumferentially about the electrode 364. In use, the electrode 360 at least partially defines the outer portion or perimeter of the ablation volume, with electrode 364 positioned at about the center of the volume, permitting current flow extending radially within the volume and between electrodes 364 and 360.

Figure 18:
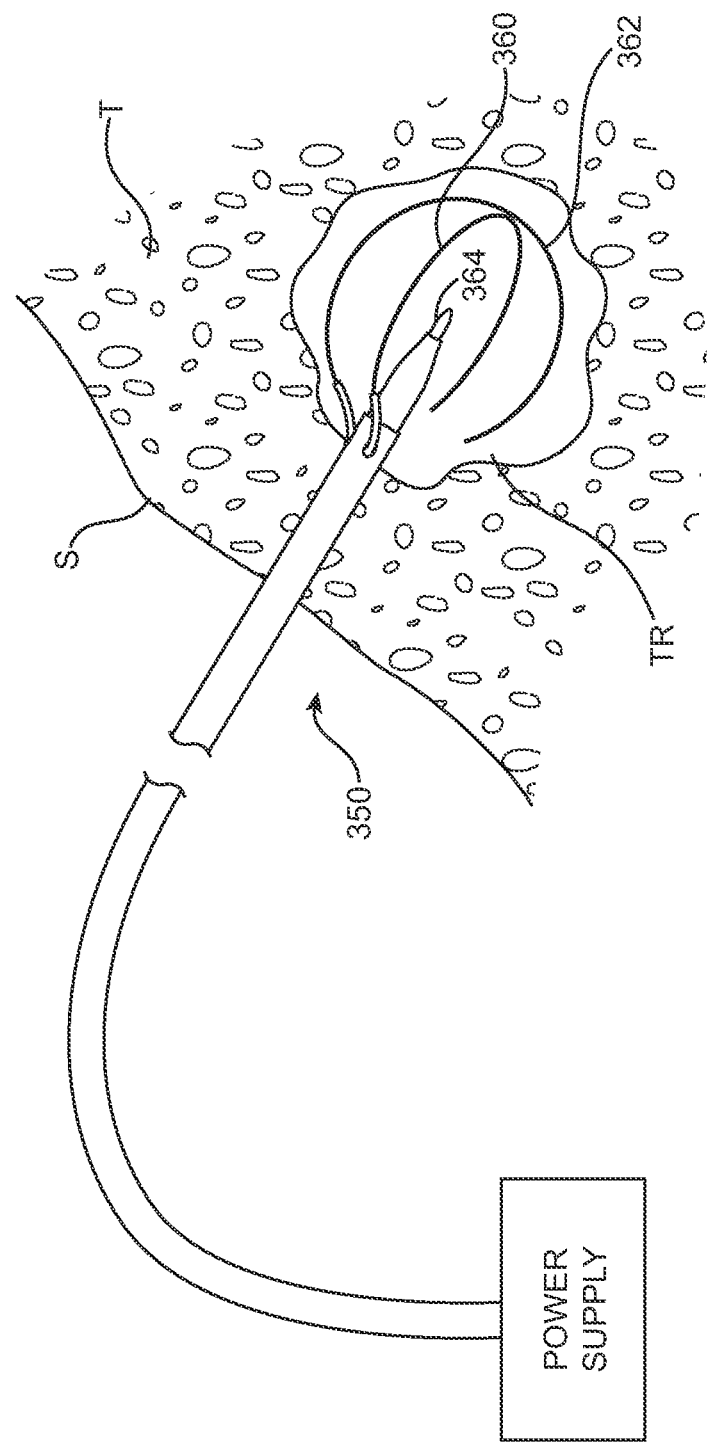
FIG. 18 shows a probe positioned in a tissue of a patient, according to an embodiment of the present invention.

FIG. 18 illustrates positioning of an ablation probe 350 as described above (e.g., FIGS. 16, 17) according to one embodiment of the present invention. The probe 350 can be introduced into a tissue, e.g., by a minimally invasive procedure, and advanced to a target tissue region ("TR"). Deployed electrodes 360, 362 at least partially define an ablation volume, and will typically include a tissue target (e.g., cancerous cells, tumor, etc.) disposed therein. The target tissue can be partially or entirely disposed in the ablation volume. Electrode 364 will by positioned approximately at the center of the ablation volume and typically at about the center of the target tissue. The probe 350 is coupled to a power supply for delivery of current to the target tissue. Power supply and/or delivered current is selected based on the desired effect and ablation treatment to be accomplished (e.g., non-thermal ablation, thermal ablation, electroporation, etc.).

Figure 19A:
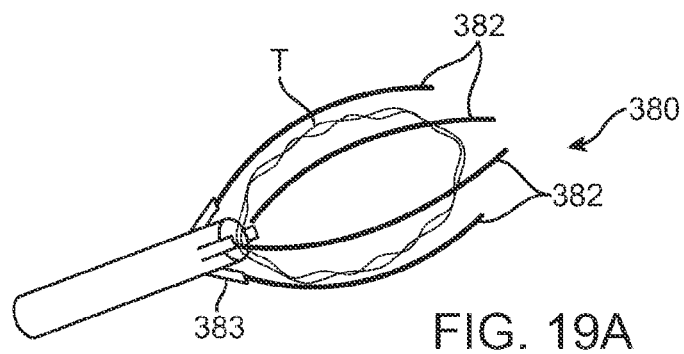
FIGS. 19A through 19D illustrate a probe according to an embodiment of the present invention, with deployment of guide tubes and associated electrodes, and field application with outer electrodes.
Figure 19B:
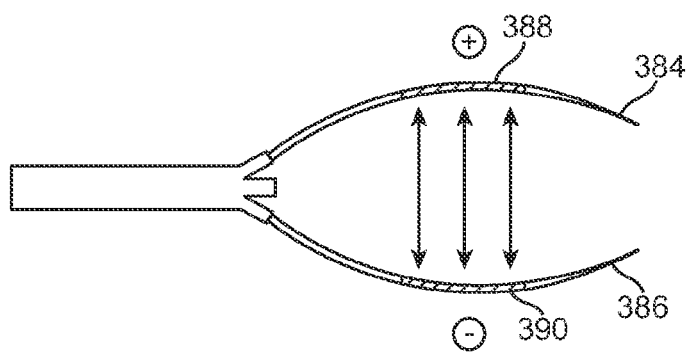
Figure 19C:
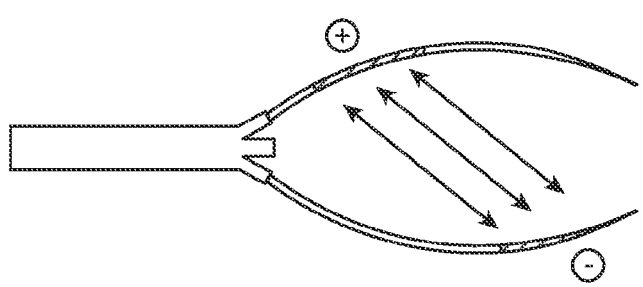
Figure 19D:
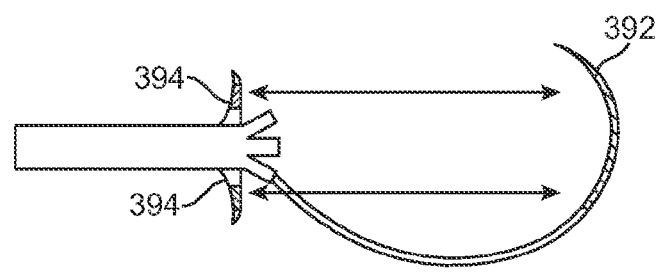

Referring to FIGS. 19A through 19D, an ablation probe/device of the present invention according to another embodiment of the present invention is described. The device 380, as illustrated in FIG. 19A, is configured for delivery of an electric field to a target tissue region ("T") such that the electric field is applied radially through target tissue region and in a plurality of different directions in the absence of a centrally positioned electrode. The device include a plurality of electrodes 382 that can be positioned to substantially define an ablation volume or target region. In some embodiments, electrodes can be deployable, e.g., from a distal portion, that can be advanced to the a target region. Similar to embodiments described above, the device 380 can include a delivery member having a lumen with guide tubes or microcatheters positioned within the lumen of a delivery member, and electrodes 382 each disposed in a microcatheter. As illustrated, microcatheter 383 can be deployed from the delivery member and may act as an initial advancement or guide tube as advanced or deployed from delivery member for initial aiming and/or positioning of electrode disposed therein. In use, treatment can include activation of electrodes 382 (e.g., opposing electrodes) in pairs, such that the electrode pairs define a circuit and an applied field extends between the two electrodes of the pair. Different electrode pairs can be activated to apply electric fields to different portions of the target tissue and/or fields having different directions/orientations. Electrodes can be configured to have defined electrically active areas, for example, by including insulated and non-insulated portions. FIG. 17B illustrates activation of opposing electrode pairs 384, 386 of a device that can include a plurality of electrode pairs, and field generation between the activated electrode pairs as illustrated by the arrows. Electrodes 381, 386 can each include active portions 388, 390, respectively. Electrodes can each include a single or continuous active area, as shown, or a plurality of active areas along a length of an electrode (not shown). Active areas can be positioned at various locations on electrodes on as to select the direction/orientation of the field applied by a given pair (see, e.g., FIG. 19C). FIG. 19D illustrates an embodiment of an electrode pair 392, 394 having an electrode configuration for generating a field that runs approximately parallel to the longitudinal axis of the probe. A device can include a plurality of electrode pairs configured as described, with different pairs of the plurality applying fields in different directions across the target tissue. Configuration and arrangement of electrodes in this manner can permit application of fields through the tumor in a plurality of different directions. Current can be applied such that fields extend substantially through an approximate central region of the volume, as shown. Though various configurations of electrodes and/or active areas on electrodes are included in the present invention, including probes/electrodes configured such that applied fields extend through a central region, or through regions of the volume other than the center, or both. Electrode pairs can be activated individually or sequentially such that only one electrode pair is activated at any one moment, or multiple pairs can be activated simultaneously.

Figure 20:
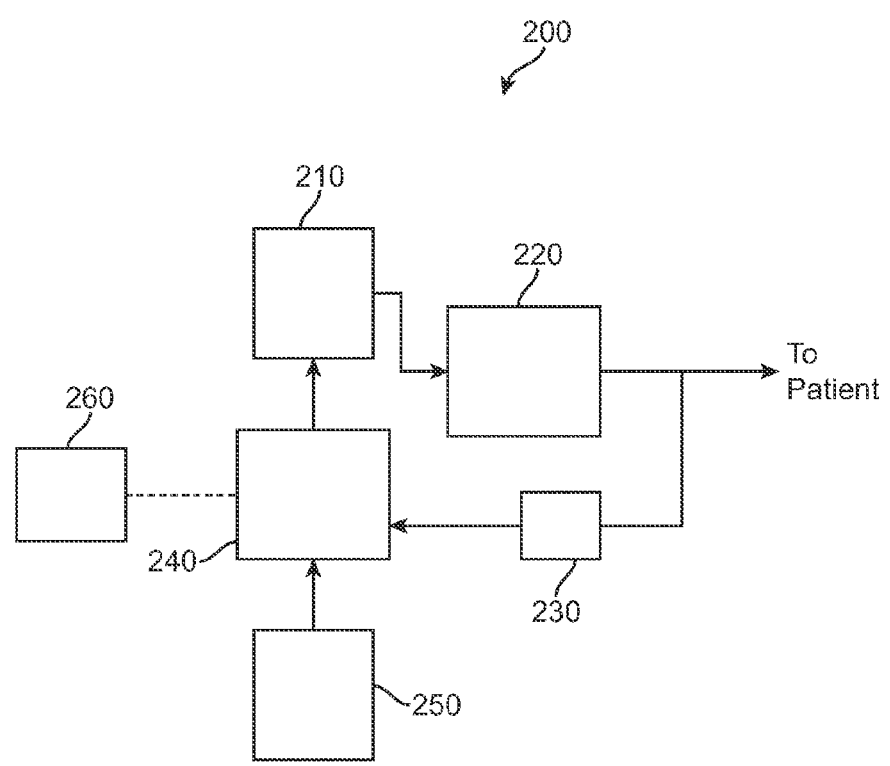
FIG. 20 illustrates a system according to an embodiment of the present invention.

A system according to an embodiment of the present invention is described with reference to FIG. 20. The system 200 can include incorporated therewith any device of the present invention for delivery of energy to the patient, and includes a power unit 210 that delivers energy to a driver unit 220 and then to electrode(s) of an inventive device. The components of the system individually or collectively, or in a combination of components, can comprise an energy source for a system of the invention. A power unit 210 can include any means of generating electrical power used for operating a device of the invention and applying electrical current to a target tissue as described herein. A power unit 210 can include, for example, one or more electrical generators, batteries (e.g., portable battery unit), and the like. One advantage of the systems of the present invention making use of non-thermal ablation techniques is the low power required for the ablation process. Thus, in one embodiment, a system of the invention can include a portable and/or battery operated device. A feedback unit 230 measures electric field delivery parameters and/or characteristics of the tissue of the target tissue region, measured parameters/characteristics including without limitation current, voltage, impedance, temperature and the like. One or more sensors (e.g., temperature sensor, impedance sensor, thermocouple, etc.) can be included in the system and can be coupled with the device or system and/or separately positioned at or within the patient's tissue. These sensors and/or the feedback unit 230 can be used to monitor or control the delivery of energy to the tissue. The power unit 210 and/or other components of the system can be driven by a control unit 240, which may be coupled with a user interface 250 for input and/or control, for example, from a technician or physician. The control unit 240 and system 200 can be coupled with an imaging system 260 (see above) for locating and/or characterizing the target tissue region and/or location or positioning the device during use.

A control unit can include a, e.g., a computer or a wide variety of proprietary or commercially available computers or systems having one or more processing structures, a personal computer, and the like, with such systems often comprising data processing hardware and/or software configured to implement any one (or combination of) the method steps described herein. Any software will typically include machine readable code of programming instructions embodied in a tangible media such as a memory, a digital or optical recovering media, optical, electrical, or wireless telemetry signals, or the like, and one or more of these structures may also be used to transmit data and information between components of the system in any wide variety of distributed or centralized signal processing architectures.

Components of the system, including the controller, can be used to control the amount of power or electrical energy delivered to the target tissue. Energy may be delivered in a programmed or pre-determined amount or may begin as an initial setting with modifications to the electric field being made during the energy delivery and ablation process. In one embodiment, for example, the system can deliver energy in a "scanning mode", where electric field parameters, such as applied voltage and frequency, include delivery across a pre-determined range. Feedback mechanisms can be used to monitor the electric field delivery in scanning mode and select from the delivery range parameters optimal for ablation of the tissue being targeted.

Methods and techniques of the present invention may employ a single device or a plurality of devices. In one embodiment, for example, a device of the present invention (e.g., device as illustrated in FIGS. 2A through 2C) can be positioned within a target tissue region as described above. A second device can then be positioned within the target tissue region or in another target tissue region, either of pan of the same tumor or at a separate tumor. In one embodiment, for example, a first device is positioned in a target tissue region, and a second device can be positioned in the target tissue region, where the second device is positioned at an angle (e.g., 90 degree angle) relative the first device.

Systems and devices of the present invention can, though not necessarily, be used in conjunction with other systems, ablation systems, cancer treatment systems, such as drug delivery, local or systemic delivery, radiology or nuclear medicine systems, and the like. Similarly, devices can be modified to incorporate components and/or aspects of other systems, such as drug delivery systems, including drug delivery needles, electrodes, etc.

While embodiments of the present invention are discussed in terms of use for non-thermal ablation and destruction of cancerous cells as described above, in some instances systems and probes can be used and/or configured for delivering energy sufficient for other types of tissue ablation, such as thermal RF ablation, microwave ablation, irreversible electroporation via high-voltage direct current, and the like. For example, a system of the invention can include a power unit configured for delivery of energy suitable for any one or more types of tissue ablations. In fact, certain probe configurations have designs (e.g., electrode arrangements) that can provide improved delivery of a various types of tissue ablation, including, e.g., improved delivery of thermal RF ablation, and the like. And treatment according to methods of the present invention can include delivery of one or more types of tissue ablations for a given treatment.

In some instances, for example, treatment may include one or more ablation delivery modes, such as one mode where non-thermal tissue ablation is delivered, which can precede or follow another ablation mode, such as thermal RF tissue ablation. For example, in one embodiment, treatment can include delivery of non-thermal tissue ablation followed by a shorter application or pulse of energy to produce a thermal mediated effect, to help "sterilize" one or more components of the probe, e.g., for withdrawal from the target tissue through the entry track and reduced risk of tracking any potentially viable cancer cells through tissue during probe withdrawal.

In some embodiments, systems of the present invention can further include certain components and aspects for positioning and/or stabilizing probes and other components during the energy delivery process. For example, in instances where a phase of treatment, such as energy application, is expected to exceed more than a few minutes, it may be desirable to include a positioning or stabilizing structure to maintain a probe in a desired position/location without specifically requiring a user (e.g., surgeon) to hand-hold the probe. Thus a system can include a harness, belt, clamp, or other structure to maintain probe positioning. Systems can be designed for ambulatory use so as to allow for movement of the patient (e.g., shifting, walking, etc.) during treatment. In fact, the low-power requirements and corresponding design options (e.g., battery powered system) may make the current systems particularly well suited for use as an ambulatory system.

In some instances, it may be desirable to remove ablated tissue from the target tissue region at a stage of the ablation process described herein. For example, it has been observed that, in some instances, removal of ablated tissue can improve treatment and/or recovery of the subject, and possibly reduce stress and/or toxicity (e.g., local tissue toxicity, systemic toxicity, etc.) associated with the ablation process of the present invention.

Various devices and methodologies can be utilized for removing the ablated tissue. In some instances, as described above, the ablated tissue can effectively "liquefy" or assume properties of a liquid-like material. The liquid ablated tissue can then be drained or removed from the target tissue region. In one embodiment, removal of the ablated tissue can be as simple as allowing ablated tissue to leak or ooze out of target tissue region (e.g., with or without application of a three or pressure to the target tissue region or tissue proximate thereto), for example, by leaking out holes or piercings in the tissue, including, e.g., entry holes through which the device/electrodes are introduced into the target tissue region. In other embodiments, removal of ablated tissue can be more deliberate or controlled. The removal can be accomplished using a device or apparatus separate from the ablation device, such as a syringe or other liquid removing device, or the removal can be accomplished using the ablation device further configured for the tissue removal. A device configured for removal of ablated tissue can include a tissue removal member, which can be deployable from a delivery catheter. In one embodiment, the removal member includes a catheter-like member having a lumen for carrying liquid. The removal member can be separate from or combined with other components of the device, such as an electrode (e.g., central electrode), delivery member, and the like. Various configurations of removal members capable of removing ablated tissue from the target tissue region will be envisioned and certain exemplary embodiments are described herein. It will also be recognized that while removal members are discussed with respect to use in removing ablated tissue from the target tissue region, in some instances, removal members may have additional or multipurpose functionality and, for example, may be additionally used to deliver an agent or material (e.g., drug, chemotherapeutic agent, flushing buffer, etc.) to the target tissue region.

As noted above, treatment as described was observed to be selective in destroying cancerous cells within a defined target tissue region. Without being bound by any particular theory, one or more reasons could explain the selective nature of the described treatment. One reason for the observed selectivity appeared to be design of the ablation probe-treatment was substantially confined to a treatment volume as defined by the positioning of the electrodes. Only the tissue is within the probe's outer electrodes appeared to receive the delivered energy and that is the area the electric field almost exclusively covers. The field does not appear to extend outside of the volume defined by the outer electrodes.

Second, selectivity may be inherent to the mechanism of cell destruction. In embodiments where low-power is applied as described above, cell ablation is distinguished from a primarily thermal-mediated ablation as performed in known high-frequency RF thermal ablation, or microwave ablation techniques, nor is the effect due to high voltage irreversible electroporation by application high voltage direct current as has been previously described elsewhere. All of these previously taught methods, by design, destroy normal tissue as well as cancer. Techniques of the present invention make use of voltage, power and frequency ranges that are not within the range of thermal or high voltage ablation.

Furthermore, without being bound to any particular theory, additional cellular-level effects of the current techniques may cause selective destruction of cancerous cells compared to non-cancerous cells. The energy application as described herein appears to mediate breakdown of the cell membrane integrity. One potential reason for the breakdown of the cell membrane and/or destruction of cancer cells may include disruption of cell cycle progression and cell mitosis by the applied electric field, with the disruption triggering cell destruction (e.g., necrosis, apoptosis, disintegration) as has been observed herein. Since cancer cells in a tumor are actively dividing and proliferating and, therefore actively, progressing through the cell cycle/mitosis at a much higher rate compared to orders of magnitude slower rates of non-cancerous or healthy cells, this energy application as described can be selective to cancer cells.

Another possible cause of cell destruction may include dielectric breakdown of the cellular membrane. Cell membranes are known to have a dielectric breakdown threshold, above which the cell is destroyed. A normal cell typically has a higher threshold than a cancer cell. Thus, it is possible to selectively breakdown a cancer cell membrane without harming a normal cell where the applied energy is above the dielectric breakdown threshold for cancerous cells but below that of normal/healthy cells. Breakdown in membrane integrity resulting from treatment as described herein may occur in both extracellular membranes as well as intracellular membranes, for example, causing rupture of lysosomes containing components (e.g., degradative enzymes, etc.) that further lead to cell destruction. Rupturing of cells and spilling of cellular contents can negatively effect nearby cells, resulting in a sort of cascade of cellular destruction. Treatment may also stimulate an immune response that can "clean up" the treatment region and may further destroy any residual/viable cancer cells not destroyed or removed. Other disruptions and/or mechanisms of action may also occur. Regardless of any particular mechanism of action, where cellular disruption occurs as described, the resulting fluid appears to further act in some instances as a sort of virtual electrode, making the electrode larger and larger in diameter, and finally substantially covering the entire target tissue region.

It is understood that the examples and embodiments described herein are for illustrative purposes only and that various modifications or changes in light thereof will be suggested to persons skilled in the art and are included within the spirit and purview of this application and scope of the appended claims. Numerous different combinations are possible, and such combinations are considered part of the present invention.

What is claimed is:

1. A method of delivering an electric field to a target tissue, the method comprising:
    advancing a treatment probe comprising a delivery member into a patient;
    advancing a guide through the lumen of the delivery member;
    deploying and advancing the guide along a guide tissue penetration path;
    deploying an electrode from the guide along an electrode tissue penetration path to define a treatment volume within the target tissue; and
    establishing an alternating electrical current flow extending within the treatment volume of the patient using the deployed electrode, wherein the alternating electrical current flow provides a voltage field of less than 50 V/cm within the treatment volume and selectively destroys abnormally proliferating cells while leaving normal cells substantially intact within the treatment volume.

2. The method of claim 1, wherein:
    the delivery member has a long axis;
    deploying the guide along the guide tissue penetration path directs advancement of the guide distally and away from the delivery member long axis; and
    deploying the electrode from the guide along the electrode tissue penetration path directs advancement of the electrode distally and parallel to or toward the delivery member long axis.

3. The method of claim 1, wherein the guide is deployed before the electrode is deployed.

4. The method of claim 1, further comprising positioning a central electrode within the treatment volume, and wherein the alternating electrical current flow extends between the central electrode and the electrode.

5. The method of claim 1, wherein advancing the treatment probe comprises penetrating the target tissue with a distal end of the delivery member.

6. The method of claim 1, wherein the alternating electrical current flow preferentially destroys cancerous cells within the treatment volume while leaving non-cancerous cells substantially intact within the treatment volume.

7. The method of claim 6, wherein the alternating electrical current flow causes heating of the treatment volume.

8. The method of claim 1, further comprising:
    deploying a second guide through an opening in a sidewall of the delivery member;
    deploying a second electrode from the second guide; and
    establishing a second alternating electrical current flow extending within the treatment volume of the patient using the deployed second electrode, wherein the second alternating electrical current flow provides a voltage field of less than 50 V/cm within the treatment volume and selectively destroys abnormally proliferating cells while leaving normal cells substantially intact within the treatment volume.

9. The method of claim 8, further comprising positioning a central electrode within the treatment volume, and wherein the alternating electrical currently flow extends between the central electrode and the electrode, and wherein the second alternating electrical current flow extends between the central electrode and the second electrode.

10. A system for preferentially destroying cancerous cells in a treatment tissue volume, the system comprising:
    a treatment probe comprising a delivery member having a long axis, a guide housed within the lumen of the delivery member and configured to be deployed from a sidewall opening of the delivery member and an electrode configured to be deployed from the guide along an electrode tissue penetration path so as to be penetrated into tissue and define a treatment volume within the treatment tissue volume; and
    an energy source coupled with the electrode to establish an alternating electrical current flow that provides a voltage field of less than 50 V/cm within the treatment tissue volume and selectively destroys abnormally proliferating cells in the treatment tissue volume while leaving normal cells in the treatment tissue volume substantially intact.

11. The system of claim 10, wherein:
    the delivery member has a long axis;
    deployment of the guide from delivery member directs advancement of the guide distally and away from the delivery member long axis; and
    deployment of the electrode from the guide directs advancement of the electrode distally and parallel to or toward the delivery member long axis.

12. The system of claim 10, wherein guide is configured to be penetrated into tissue.

13. The system of claim 12, wherein the delivery member is configured to be penetrated into tissue.

14. The system of claim 10, wherein the treatment probe comprises a central electrode configured to be positioned within the treatment tissue volume, and wherein the alternating electrical current flow extends between the central electrode and the electrode.

15. The system of claim 10, wherein the alternating electrical current flow causes heating of tissue within the treatment tissue volume.

16. The system of claim 10, further comprising a control system operatively coupled to the energy source and the treatment probe, the control system comprising:
- one or more processors; and
- memory including instructions stored thereon that, when executed by the one or more processors, cause the control system to provide, via at least the energy source and the electrode, the alternating electrical current flow within the treatment tissue volume.

17. The system of claim 16, further comprising a feedback unit for detecting a characteristic of tissue within the treatment tissue volume.

18. The system of claim 17, wherein the characteristics comprises impedance or temperature.

* * * * *